US011083386B2

United States Patent
Hu et al.

(10) Patent No.: US 11,083,386 B2
(45) Date of Patent: Aug. 10, 2021

(54) WIRELESS INTRACRANIAL MONITORING SYSTEM

(71) Applicant: BRANCHPOINT TECHNOLOGIES, INC., Irvine, CA (US)

(72) Inventors: Nicholas Hu, Irvine, CA (US); Kevin Hughes, Aliso Viejo, CA (US); Hyung Phouasalit, Irvine, CA (US)

(73) Assignee: Branchpoint Technologies, Inc., Irvine, CA (US)

( * ) Notice: Subject to any disclaimer, the term of this patent is extended or adjusted under 35 U.S.C. 154(b) by 414 days.

(21) Appl. No.: 15/893,290

(22) Filed: Feb. 9, 2018

(65) Prior Publication Data

US 2018/0242864 A1   Aug. 30, 2018

Related U.S. Application Data

(63) Continuation of application No. 14/885,884, filed on Oct. 16, 2015, now Pat. No. 9,901,269, which is a
(Continued)

(51) Int. Cl.
*A61B 5/03*   (2006.01)
*A61B 5/01*   (2006.01)
(Continued)

(52) U.S. Cl.
CPC ............ *A61B 5/031* (2013.01); *A61B 5/0031* (2013.01); *A61B 5/01* (2013.01); *A61B 5/036* (2013.01);
(Continued)

(58) Field of Classification Search
CPC .. A61B 5/031; A61B 5/01; A61B 5/72; A61B 5/11; A61B 5/6852; A61B 5/0031;
(Continued)

(56) References Cited

U.S. PATENT DOCUMENTS 3,434,090 A   3/1969 Chelner
3,757,770 A   9/1973 Baryshaw et al.
(Continued)

FOREIGN PATENT DOCUMENTS

EP   1 491 137    12/2004
JP   2002-010986   1/2002
(Continued)

OTHER PUBLICATIONS

Fujiwara et al., Oct. 1, 1989, Impact-induced intracranial pressure caused by an accelerated motion of the head or by skull deformation: an experimental study using physical models of the head and neck, and ones of the skull, Forensic Science International, 43(2):159-169.
(Continued)

*Primary Examiner* — Sean P Dougherty
(74) *Attorney, Agent, or Firm* — Knobbe, Martens, Olson & Bear, LLP

(57) ABSTRACT

Systems and methods for monitoring physiological parameters such as intracranial pressure ("ICP"), intracranial temperature, and subject head position are provided. In some embodiments, an implantable apparatus for measuring ICP can be implanted into a subject skull. The apparatus can comprise an implant body having a hermetically sealed chamber housing a gas at a reference pressure, and a pressure conduction catheter having a proximal end and a distal end, wherein the distal end is configured to extend into the brain through a burr hole in the skull and includes a plurality of ports. A barrier can cover the ports of the distal end of the pressure conduction catheter, wherein the barrier and pressure conduction catheter are filled with a number of gas molecules so that the barrier is not in tension in a predefined range of ICPs. The ports may also be configured such that a barrier is not necessary. Standoffs on the body
(Continued)

may be included that stabilize the implant on the skull and enhance reliability and robustness of the measurements.

21 Claims, 24 Drawing Sheets

Related U.S. Application Data continuation-in-part of application No. 14/688,799, filed on Apr. 16, 2015, now Pat. No. 9,848,789.

(60) Provisional application No. 61/981,103, filed on Apr. 17, 2014.

(51) Int. Cl.
   *A61B 5/00* (2006.01)
   *A61B 5/11* (2006.01)
   *A61B 90/11* (2016.01)
   *A61B 90/10* (2016.01)

(52) U.S. Cl.
   CPC .................. *A61B 5/11* (2013.01); *A61B 5/72* (2013.01); *A61B 90/11* (2016.02); *A61B 5/6852* (2013.01); *A61B 2090/103* (2016.02); *A61B 2560/0257* (2013.01)

(58) Field of Classification Search
   CPC ............ A61B 5/036; A61B 2560/0257; A61B 2090/103; A61B 90/11
   See application file for complete search history.

(56) References Cited

U.S. PATENT DOCUMENTS

| | | | |
|---|---|---|---|
| 4,014,319 A | 3/1977 | Favre | |
| 4,026,276 A | 5/1977 | Chubbuck | |
| 4,062,354 A | 12/1977 | Taylor et al. | |
| 4,080,653 A | 3/1978 | Barnes, Jr. et al. | |
| 4,114,603 A | 9/1978 | Wilkinson | |
| 4,114,606 A | 9/1978 | Seylar | |
| 4,127,110 A | 11/1978 | Bullara | |
| 4,147,161 A | 4/1979 | Lkebe et al. | |
| 4,186,749 A | 2/1980 | Fryer | |
| 4,206,762 A | 6/1980 | Cosman | |
| 4,237,900 A | 12/1980 | Schulman et al. | |
| 4,246,908 A | 1/1981 | Inagaki et al. | |
| 4,265,252 A | 5/1981 | Chubbuck et al. | |
| 4,281,666 A | 8/1981 | Cosman | |
| 4,354,506 A | 10/1982 | Sakaguchi et al. | |
| 4,385,636 A | 5/1983 | Cosman | |
| 4,471,786 A | 9/1984 | Inagaki et al. | |
| 4,494,411 A | 1/1985 | Koschke et al. | |
| 4,519,401 A | 5/1985 | Ko et al. | |
| 4,600,013 A | 7/1986 | Landy et al. | |
| 4,660,568 A * | 4/1987 | Cosman ............... | A61B 5/0002 600/561 |
| 4,738,267 A * | 4/1988 | Lazorthes ............. | G01L 9/0051 600/561 |
| 5,291,899 A | 3/1994 | Watanabe et al. | |
| 5,573,007 A | 11/1996 | Bobo | |
| 5,579,774 A | 12/1996 | Miller et al. | |
| 5,873,840 A * | 2/1999 | Neff ....................... | A61B 5/031 600/561 |
| 5,987,995 A * | 11/1999 | Sawatari ............... | A61B 5/0215 600/480 |
| 5,993,395 A | 11/1999 | Shulze | |
| 6,033,366 A * | 3/2000 | Brockway ............ | A61B 5/0215 600/435 |
| 6,113,553 A | 9/2000 | Chubbuck | |
| 6,117,086 A * | 9/2000 | Shulze ................. | A61B 5/0215 600/486 |
| 6,231,524 B1 | 5/2001 | Wallace et al. | |
| 6,234,973 B1 | 5/2001 | Meader et al. | |
| 6,248,080 B1 | 6/2001 | Miesel et al. | |
| 6,409,674 B1 | 6/2002 | Brockway et al. | |
| 6,533,733 B1 | 3/2003 | Ericson et al. | |
| 6,673,022 B1 | 1/2004 | Bobo | |
| 6,731,976 B2 | 5/2004 | Penn et al. | |
| 6,855,115 B2 | 2/2005 | Fonseca et al. | |
| 6,897,788 B2 | 5/2005 | Khair et al. | |
| 6,950,699 B1 | 9/2005 | Manwaring et al. | |
| 7,025,727 B2 | 4/2006 | Brockway et al. | |
| 7,122,007 B2 | 10/2006 | Querfurth | |
| 7,198,602 B2 | 4/2007 | Eide | |
| 7,212,864 B2 | 5/2007 | Wahlstrand et al. | |
| 7,245,117 B1 | 7/2007 | Joy et al. | |
| 7,335,162 B2 | 2/2008 | Eide | |
| 7,347,822 B2 | 3/2008 | Brockway et al. | |
| 7,425,200 B2 | 9/2008 | Brockway et al. | |
| 7,481,774 B2 | 1/2009 | Brockway et al. | |
| 7,621,878 B2 | 11/2009 | Ericson et al. | |
| 7,780,679 B2 | 8/2010 | Bobo | |
| RE42,378 E | 5/2011 | Wolinsky et al. | |
| 8,016,763 B2 | 9/2011 | Eide | |
| 8,109,899 B2 | 2/2012 | Sundström et al. | |
| 8,237,451 B2 | 8/2012 | Joy et al. | |
| 8,343,068 B2 | 1/2013 | Najafi et al. | |
| 8,454,701 B2 | 6/2013 | Devauchelle et al. | |
| 8,457,744 B2 | 6/2013 | Janzig et al. | |
| 8,506,514 B2 | 8/2013 | Pedersen et al. | |
| 9,232,921 B2 | 1/2016 | Bobo | |
| 9,636,017 B2 | 5/2017 | Dextradeur et al. | |
| 9,848,789 B2 * | 12/2017 | Hu .......................... | A61B 5/031 |
| 9,901,268 B2 | 2/2018 | Hughes et al. | |
| 9,901,269 B2 * | 2/2018 | Hu .......................... | A61B 5/031 |
| 10,123,713 B2 * | 11/2018 | Gohler ................. | A61B 5/0031 |
| 2002/0151816 A1 | 10/2002 | Rich et al. | |
| 2002/0169382 A1 * | 11/2002 | Bobo, Sr. ............... | A61B 5/031 600/486 |
| 2002/0177782 A1 * | 11/2002 | Penner ................... | A61B 5/031 600/485 |
| 2003/0216666 A1 | 11/2003 | Ericson et al. | |
| 2005/0061079 A1 | 3/2005 | Schulman | |
| 2005/0203438 A1 | 9/2005 | Manwaring et al. | |
| 2006/0025704 A1 | 2/2006 | Stendel et al. | |
| 2006/0206037 A1 | 9/2006 | Braxton | |
| 2007/0088223 A1 | 4/2007 | Mann et al. | |
| 2007/0244411 A1 | 10/2007 | Jeng et al. | |
| 2008/0139959 A1 | 6/2008 | Miethke et al. | |
| 2008/0161659 A1 | 7/2008 | Reichenberger et al. | |
| 2008/0262319 A1 | 10/2008 | Reichenberger et al. | |
| 2008/0269573 A1 | 10/2008 | Najafi et al. | |
| 2009/0143656 A1 | 6/2009 | Manwaring et al. | |
| 2009/0143696 A1 | 6/2009 | Najafi et al. | |
| 2009/0203983 A1 | 8/2009 | Carlton et al. | |
| 2009/0216149 A1 | 8/2009 | Neff et al. | |
| 2009/0270759 A1 * | 10/2009 | Wilson .................. | A61B 5/742 600/561 |
| 2010/0030103 A1 | 2/2010 | Lutze et al. | |
| 2010/0063542 A1 | 3/2010 | van der Burg et al. | |
| 2010/0121213 A1 | 5/2010 | Giftakis et al. | |
| 2010/0161004 A1 | 6/2010 | Najafi et al. | |
| 2010/0204589 A1 | 8/2010 | Swoboda et al. | |
| 2010/0217108 A1 | 8/2010 | Tauber et al. | |
| 2010/0262036 A1 | 10/2010 | Najafi et al. | |
| 2011/0009716 A1 | 1/2011 | Gohler et al. | |
| 2011/0066072 A1 | 3/2011 | Kawoos et al. | |
| 2011/0071457 A1 | 3/2011 | Raman | |
| 2011/0224595 A1 | 9/2011 | Pedersen et al. | |
| 2012/0265028 A1 * | 10/2012 | Hughes ................. | A61B 5/1117 600/301 |
| 2012/0302938 A1 | 11/2012 | Browd et al. | |
| 2013/0041271 A1 | 2/2013 | Ben-Ari et al. | |
| 2014/0005569 A1 * | 1/2014 | Miethke .............. | G01L 19/0038 600/561 |
| 2014/0296687 A1 * | 10/2014 | Irazoqui ................ | A61B 5/686 600/398 |

(56) References Cited

U.S. PATENT DOCUMENTS

2018/0103863 A1   4/2018  Hu et al.
2018/0249920 A1   9/2018  Hughes et al.

FOREIGN PATENT DOCUMENTS

| JP | 2005-512663 | 5/2005 |
| JP | 2009-112839 | 5/2009 |
| WO | WO 02/05710 | 1/2002 |
| WO | WO 03/053234 | 7/2003 |
| WO | WO 12/112819 | 8/2012 |

OTHER PUBLICATIONS

Yanagida et al., Apr. 1, 1989, Differences in the intracranial pressure caused by a 'blow' and.or a 'fall'—An experimental study using physical models of the head and neck, Forensic Science International, 41(1-2):135-145.
International Search Report and Written Opinion dated Sep. 2, 2015 in PCT/US15/26219.
International Search Report and Written Opinin dated Nov. 7, 2016 in PCT/US16/048975.
Extended European Search Report dated Nov. 13, 2017 in patent application No. 15780644.9.

\* cited by examiner

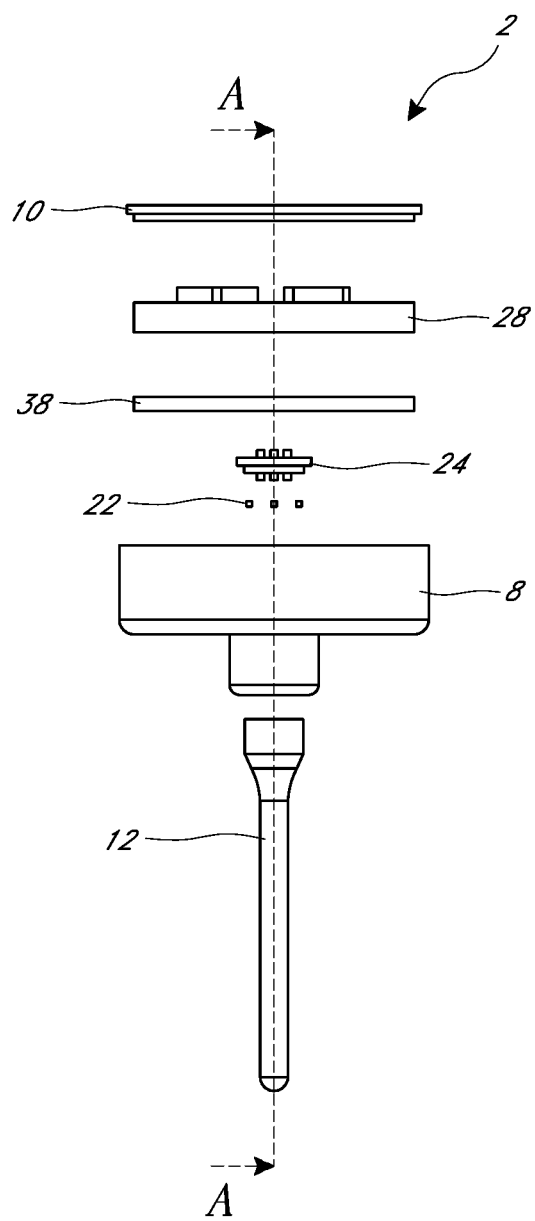
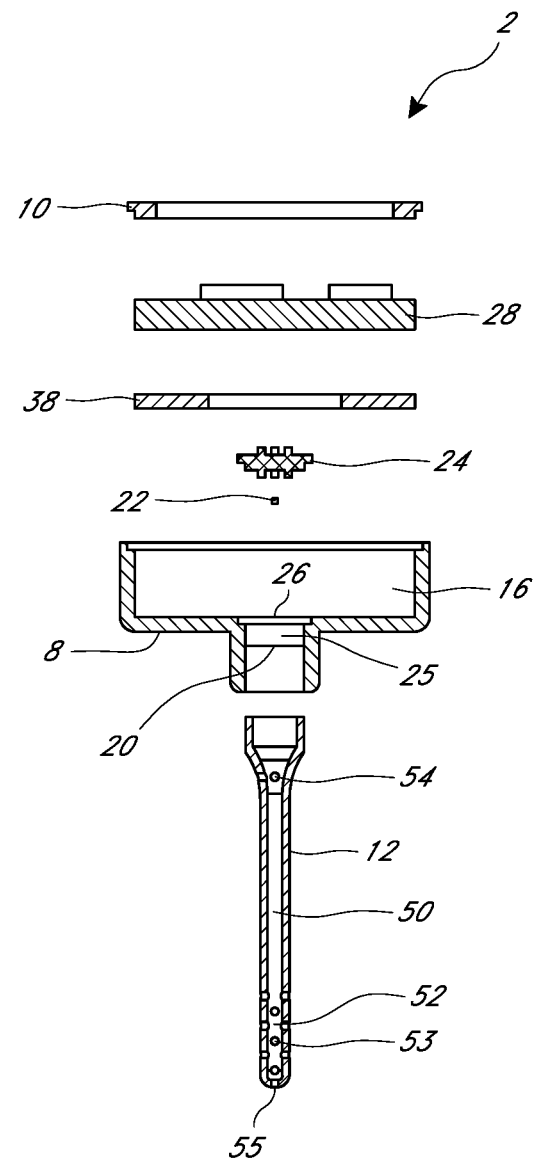
FIG. 5A
FIG. 5B

WIRELESS INTRACRANIAL MONITORING SYSTEM

INCORPORATION BY REFERENCE TO ANY PRIORITY APPLICATIONS

Any and all applications, for which a foreign or domestic priority claim is identified in the Application Data Sheet as filed with the present application, are hereby incorporated by reference. This application is a continuation of U.S. patent application Ser. No. 14/885,884, entitled "WIRELESS INTRACRANIAL MONITORING SYSTEM," and filed on Oct. 16, 2015, which is a continuation-in-part of U.S. patent application Ser. No. 14/688,799, entitled "WIRELESS INTRACRANIAL MONITORING SYSTEM," and filed on Apr. 16, 2015, which claims the benefit of U.S. Provisional Patent Application No. 61/981,103, entitled "WIRELESS INTRACRANIAL MONITORING SYSTEM," and filed on Apr. 17, 2014, the entire contents of each of which are incorporated herein by reference.

BACKGROUND

The present invention is directed to the field of implantable medical devices, and more specifically, medical devices for monitoring physiological parameters of a subject head.

SUMMARY

Example embodiments described herein have innovative features, no single one of which is indispensable or solely responsible for their desirable attributes. Without limiting the scope of the claims, some of the advantageous features will now be summarized.

In some cases, monitoring physiological parameters of a subject head can be desirable. For example, it can be desirable to measure the intracranial pressure ("ICP") of a patient who has brain tumors, hydrocephalus, meningitis, Reye syndrome, and/or other conditions, or has suffered a head injury and/or head trauma. Conventional systems and methods of measuring ICP utilize a fluid column established between a patient's ventricle and an external scale. The scale can be positioned at the same height from the floor as the tip of the catheter in the ventricles. The ICP can then be read based on the fluid levels in the fluid column. Electronic transducers can be coupled to the fluid column to provide digital readouts of the data. Variations of this technology include utilizing a catheter that contains a sealed gas bladder, and measuring the pressure read on the external end of the bladder.

These conventional methods can suffer from a number of problems. For example, the pressure measurements taken by these conventional methods can be inaccurate because they fail to take into account factors such as head temperature, barometric pressure, and patient position. The measurements can also be susceptible to noise and other measurement drift, which can include systemic errors in measurements due to changes in the measuring apparatus and/or measuring environment. The methods can also be overly invasive, restrictive, and/or uncomfortable to patients. Thus, notwithstanding the efforts of the prior art, there remains a need for providing improved systems and methods for measuring ICP and other physiological parameters.

Some embodiments of the present disclosure comprise systems and methods for monitoring physiological parameters such as ICP, intracranial temperature, and subject head position. In some embodiments, the system can comprise an implant, transceiver, and receiver interface.

In some embodiments, the implant can comprise an implant body positioned in the head of a patient. In some embodiments, a pressure conduction catheter having a fluid and/or gas column can extend from the implant body (e.g., in a distal direction). This catheter can extend from the implant body axially into a hole in a patient's skull, into the brain. In some embodiments, the catheter can have one or more ports (e.g., perforations, apertures, windows, holes, punctures, etc.) along its side wall. The ports can be covered by a barrier.

The implant body can comprise titanium and/or any biocompatible materials. For example, and without limitation, biocompatible materials as used herein can include stainless steel, Nickel-Titanium, Cobalt-Chromium, Pyrolytic Carbon, Nitinol, polymer materials (e.g., polyether ether ketone ("PEEK")) and/or other suitable implant materials. The implant body can comprise a pressure-sensing diaphragm and sensors on the side of the implant body proximal to the pressure conducting catheter. The sensors can include optical sensors, strain gauges, capacitive sensors, Hall Effect sensors, and the like, and can measure stress and/or strain and/or deflection of the pressure-sensing diaphragm. In some cases, such measurements can be used to measure deformation of the diaphragm. The diaphragm can be configured to deform in response to (based on) at least in part changes in ICP. Other sensors, such as temperature sensors, oxygen sensors, pH sensors, internal pressure sensors (e.g., measuring the pressure within the implant body) and the like, can also be used. In some embodiments, the measurement of physiological parameters such as temperature can assist in determining ICP. Temperature sensors can be configured to measure the temperatures of the implant and/or implant environment. Temperature sensors can be calibrated to body temperature (e.g., 37 degrees Celsius) and/or configured to actively measure temperatures. Actively measuring temperatures may be desirable for some implants because the implant may be used in a hypothermic environment (e.g., 25 degrees to 35 degrees Celsius) and/or an environment not based on body temperature. A reference pressure can be housed within the implant body either in the main chamber of the implant body or within a separate chamber proximal to the pressure-sensing diaphragm. The reference pressure can be a gas of known pressure put into the hermetically sealed chamber. The gas can be any suitable gas. In some cases, it can be desirable for the gas to be non-reactive and/or biocompatible. In some embodiments, the gas can also be incompressible.

The implant can further comprise a wireless data antenna and wireless power receiving coil. In some embodiments, the wireless data antenna and wireless power receiving coil can be positioned on the side of the implant body distal to the pressure conducting catheter. The implant body can be hermetically sealed, wherein electronics (e.g., an electronics assembly and/or a printed circuit board assembly ("PCBA")) for processing data within the implant body can connect to the wireless data antenna and wireless receiving coil through a hermetic feedthrough.

In some embodiments, the implant communicates with a transceiver, which can receive data (e.g., measurements) from the implant. The transceiver can process the data from the implant by applying computations, executing analytical algorithms, tagging data, and the like. The transceiver can have a user interface that enables user input and provides visual and/or output display during system operation.

In some embodiments, the implant can communicate with a receiver interface, which can interface with external systems, such as computers, electronic health record systems, mobile phones, patient monitors, and the like, for display, storage, analysis, and so forth. The implant can send data (e.g., measurements) to the receiver interface.

BRIEF DESCRIPTION OF THE DRAWINGS

FIG. 5A-B illustrates a front-exploded and cross-sectional view of the example implant illustrated in FIG. 4.

DETAILED DESCRIPTION

Although certain embodiments and examples are disclosed herein, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process can be performed in any suitable sequence and are not necessarily limited to any particular disclosed sequence. Various operations can be described as multiple discrete operations in turn, in a manner that can be helpful in understanding certain embodiments; however, the order of description should not be construed to imply that these operations are order dependent. Additionally, the structures described herein can be embodied as integrated components or as separate components. For purposes of comparing various embodiments, certain aspects and advantages of these embodiments are described. Not necessarily all such aspects or advantages are achieved by any particular embodiment. Thus, for example, various embodiments can be carried out in a manner that achieves or optimizes one advantage or group of advantages as taught herein without necessarily achieving other aspects or advantages as can also be taught or suggested herein.

The disclosed systems and methods for monitoring physiological parameters, such as ICP, intracranial temperature, and subject head position either independently or in conjunction, advantageously enable more accurate and/or less invasive monitoring of physiological pressures, better drift stability, increased versatility in monitoring locations, increased versatility in sizes of monitored regions, better compensation for other factors affecting sensor measurement, and better calibration of sensors. Disclosed systems and methods also provide magnetic resonance imaging ("MRI") safety (e.g., MRI compatibility) for measuring said physiological parameters. Additionally, disclosed systems and methods provide for ease of configuration and plug-and-playability for devices implantable in the brain.

Some embodiments of this disclosure can measure ICP, intracranial temperature, and/or head position (e.g., by head position monitoring). These parameters can be measured separately or in combination. These parameters can also be measured in conjunction with any one or combination of other physiological phenomena such as heart rate, respiratory rate, core body temperature, tissue oxygenation, and the like, as well as non-physiological phenomena, like barometric pressure, environmental temperature, time and the like.

Figure 1:
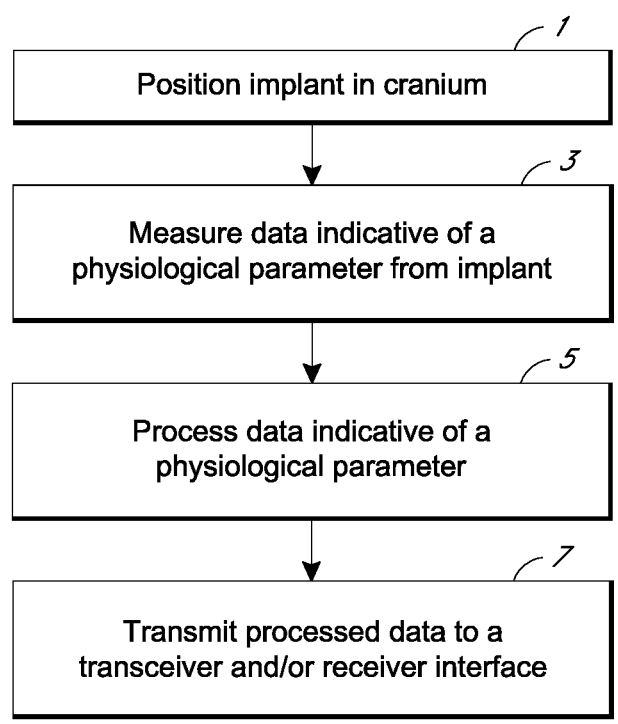
FIG. 1 illustrates a high-level flowchart of an example method of monitoring a physiological parameter of the brain.

FIG. 1 illustrates a high-level flowchart of an example method of monitoring a physiological parameter, which as used herein can include, without limitation, ICP, intracranial temperature, subject head position, orientation, oxygen levels, pH, and the like. In block 1, an implant can be positioned in the cranium. For example, an implant body can be implanted on the outer table of the skull but underneath the skin. A pressure conduction catheter can be coupled to the implant body and extend through a cranial burr hole into the epidural, subdural, parenchymal, or ventricular space. The burr hole can be large enough that the pressure conduction catheter can be advanced in an axial direction through the hole into the brain. The burr hole can be small enough such that the implant body may be too large to pass through the burr hole.

In block 3, data indicative of a physiological parameter from the implant can be measured. In some embodiments, the physiological parameter can be measured by a sensor that directly or indirectly measures the physiological parameter. For example, in some cases, a pressure can be directly measured by a pressure gauge. In other cases, for example, pressure can be indirectly measured by measuring changes in electrical resistance of a strain gauge measuring the strain of a diaphragm that can be configured to respond to changes in ICP. For example and without limitation, a diaphragm can be configured to deform in response to, at least in part, changes in ICP along the length of a pressure conduction catheter and/or ICP at a barrier covering at least a portion of the pressure conduction catheter.

In block 5, the data indicative of a physiological parameter can be processed. This can be performed by electronic circuitry (e.g., a controller and/or processor and/or hard-coded logic) operably coupled to the implant. In some cases, this circuitry can be disposed within the implant. In other cases, this circuitry can be located outside of the implant. Processing can include applying computations, executing analytical algorithms, tagging data, and the like. For example, and without limitation, computations can include integration, addition, multiplication, division, subtraction, rectification, upscaling, downscaling, derivation, time-scaling, correlation, convolution, and/or any mathematical operation and/or signal processing. Processing can also include determining the physiological parameter from the data indicative of the physiological parameter. Such determination may use look-up tables or mathematical relationships between the measurements and the physiological parameters.

In block 7, the processed data can be transmitted to a transceiver and/or receiver interface. A person having ordinary skill in the art should appreciate that the measured data can also be directly transmitted to the transceiver and/or receiver interface, and processing (e.g., the processing described referring to block 5) can occur in the transceiver and/or receiver interface. Transceivers can have a user interface that enables user input and provides visual and/or output display during system operation. Receiver interfaces can interface with external systems, such as computers, electronic health record systems, mobile phones, patient monitors, and the like, for display, storage, analysis, and so forth of physiological data monitored by the disclosed system.

Figure 2:
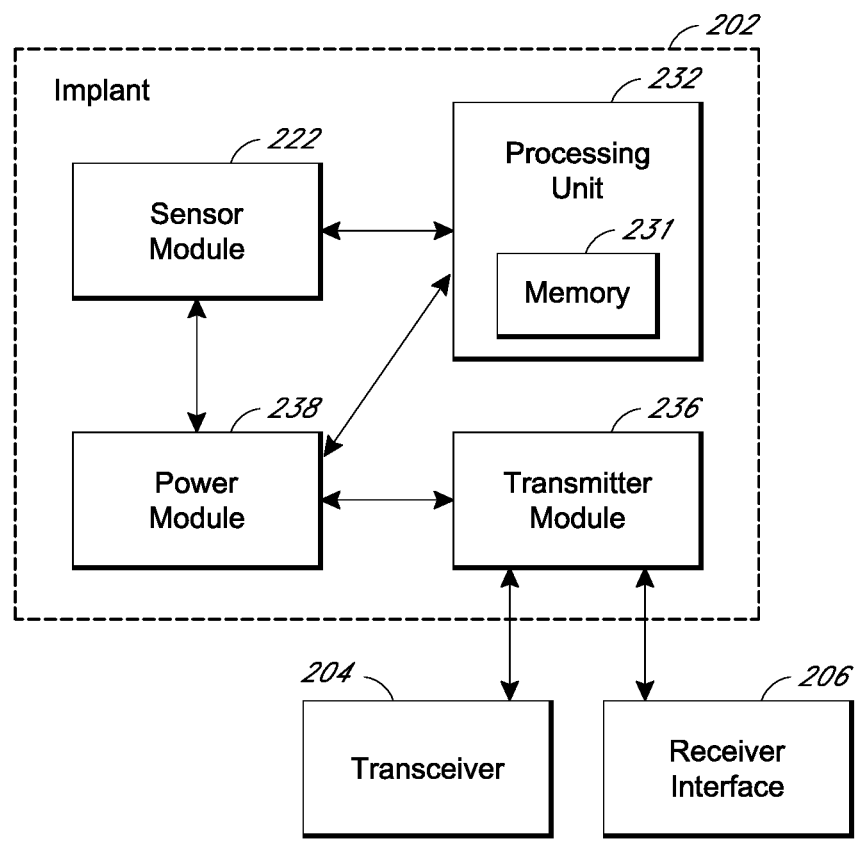
FIG. 2 illustrates a functional block diagram of an example implant system for measuring a physiological parameter of the brain.

FIG. 2 illustrates a functional block diagram of an example implant system for measuring a physiological parameter. Implant 202 can be configured for positioning in a cranium. Implant 202 can comprise sensor module 222, which may comprise sensors. Some examples of sensors include, but are not limited to, optical sensors, strain gauges, capacitive sensors, Hall Effect sensors, and the like. Sensors can measure one or a combination of ICP, intracranial temperature, subject head position, orientation, oxygen levels, pH, any physiological parameter, and the like.

Sensor module 222 can be in active communication with processing unit 232 (e.g., a controller, processor, and/or central processing unit ("CPU")), which can include memory 231. Memory 231 can contain both read-only memory ("ROM") and random access memory ("RAM"), and can provide instructions and data to processing unit 231. A portion of memory 231 can include non-volatile random access memory ("NVRAM"). Processing unit 232 typically performs logical and arithmetic operations based on program instructions stored within working memory 231.

Instructions in memory 231 can be executable to implement the methods described herein. Processing unit 232 can be in active communication with power module 238 and transmitter module 236. Power module 238 can be used to power processing unit 232, transmitter module 236, sensor module 222, and/or any other component in implant 202. Transmitter module 236 can wirelessly transmit data (e.g., from processor unit 232) from implant 202 to transceiver 204 and/or receiver interface 206.

Transceiver 204 can be a device with a user interface that enables user input and provides visual and/or output display during system operation. Receiver interface 206 can be a device communicatively coupled to an external system to monitor and/or process physiological data from implant 202.

Figure 3:
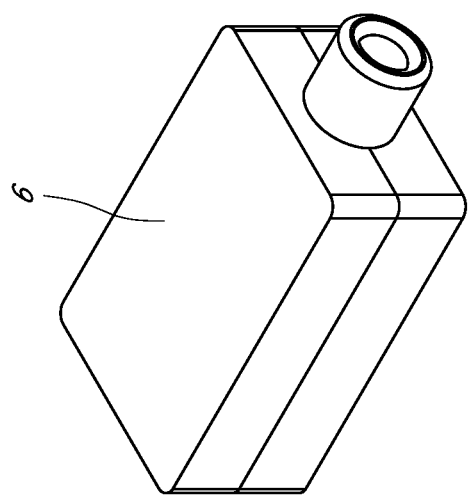
FIG. 3 illustrates example components of a system for measuring a physiological parameter, including an implant, transceiver, and receiving device.
Figure 3:
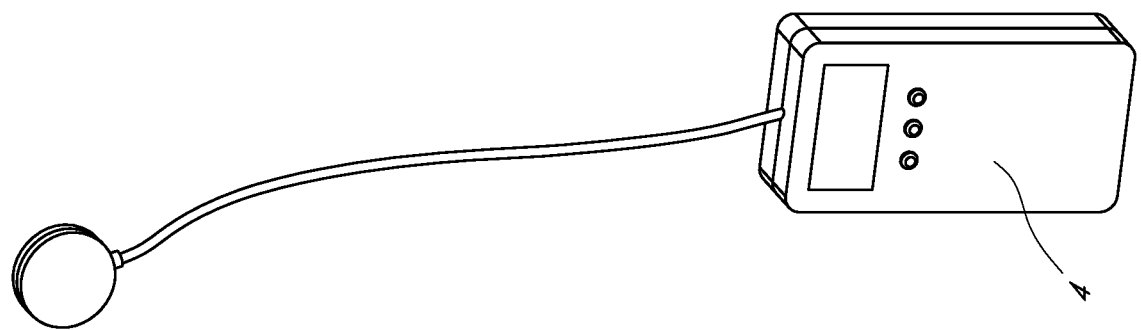
Figure 3:
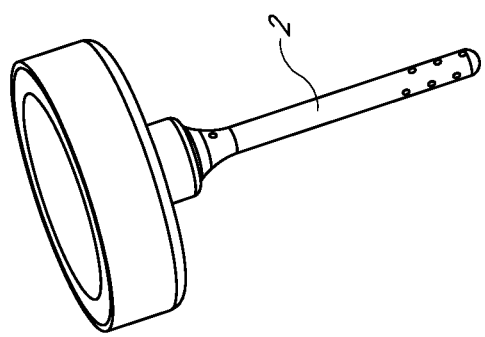

FIG. 3 illustrates example components of a system for measuring a physiological parameter, including an implant 2, transceiver 4, and receiving interface 6. Implant 2 can be either fully or partially implanted into a subject to monitor one or multiple physiological parameters. A single implant 2 can be implanted, or a plurality of implants (e.g., a plurality of implants substantially similar to implant 2). Implant 2 can be configured to wirelessly communication with other implants, transceiver 4, and/or receiver interface 6.

Transceiver 4 can be deployed to be on-demand or in periodic, intermittent or continuous operation with implant 2, as desired for on-demand data acquisition, or to download stored data from implant 2. Transceiver 4 can be also capable of wired or wireless communication with other transceivers, implants, and receiver interfaces. Transceiver 4 can be also configured to process physiological data received from implant 2, such as by applying computations, executing analytical algorithms, tagging data, and the like. Transceiver 4 can also be capable of handling data received from implant 2 for further transmissions, storage, display, or a combination thereof. Transceiver 4 can also provide visual, tactile, and auditory user interface with users to enable user input and visual and/or audio output display during system operation. Transceiver 4 can also be configured to program implant 2. For example, transceiver 4 can transmit operative instructions, software, software/firmware updates, control signals, etc.

Receiver interface 6 can be capable of wired or wireless communication with other receiver interfaces, implants, and transceivers. Receiver interface 6 can interface with external systems, such as computers, electronic health record systems, mobile phones, patient monitors, and the like, for display, storage, analysis, and so forth of physiological data monitored by the disclosed system.

In some embodiments, implant 2 can be capable of wireless communication with one or two or more or multiple transceivers (e.g., transceiver 4), one or multiple receiver interfaces (e.g., receiver interface 6), other implants (e.g., implants substantially similar to implant 2), or a combination thereof. In some embodiments, implant 2 communicates solely with a single transceiver 4 that then relays the communications in raw or processed form to other transceivers, receiver interfaces, implants or a combination thereof. In some embodiments, implant 2 communicates directly to a telemetry interface, such as Bluetooth, zigbee, Wi-Fi, or the like, of external systems, such as computers, smart phones, tablets, data capture systems, mobile telecommunications networks, or the like, without transceiver 4 or receiver interface 6 intermediaries. Wireless communication among multiple implants, transceivers, and receiver interfaces can occur sequentially, simultaneously, or both.

Figure 4:
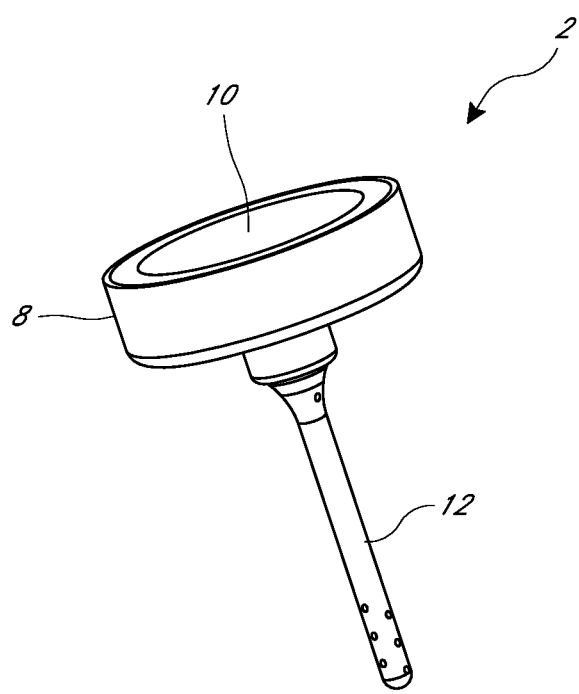
FIG. 4 illustrates a perspective view of an example implant.

FIG. 4 illustrates a perspective view of an example implant. In some embodiments, implant 2 can be configured for ICP monitoring. Implant 2 can comprise implant body 8, cap 10, and pressure conduction catheter 12. As depicted in FIG. 5A-5B, which illustrate an exploded and cross-sectional view (along line A) of implant 2. Implant body 8 can house an electronics assembly 28 (e.g., a PCBA) and a power source 38 within a first internal cavity 16 that can be hermetically sealed by a cap 10 on one end and can be sealed by a hermetic feedthrough 24 on the other end. The hermetic feedthrough 24 can enable electrical connections from electronics assembly 28 to components 22 in second internal cavity 25 or outside of implant body 8 while maintaining a hermetic seal. Hermetic seals can allow for negligible fluid and gas exchange into internal cavities 16, 25, and protect internal components from damage. Second internal cavity 25 can be formed by the wall of implant body 8, hermetic feedthrough 24 and pressure sensitive diaphragm 20. Sensors 22 are disposed within the second internal cavity 25 to detect presence or magnitude of diaphragm 20 deflection caused by pressure on the external side of diaphragm 20. One or two or more of either the same type of sensors 22 or different types of sensors can be disposed within second internal cavity 25. Some examples of sensors include, but are not limited to, optical sensors, strain gauges, capacitive sensors, Hall Effect sensors, and the like. Implant 2 can have a pressure conduction catheter 12 that couples diaphragm 20 to the region targeted for pressure measurement. In some embodiments, catheter 12 may not be incorporated, and diaphragm 20 can be positioned directly at the region targeted for pressure measurement.

In some embodiments, there can be no second internal cavity 25 in implant body 8 and/or no diaphragm 20. For example, in some embodiments, as will also later be described, implant body 8 may not have internal cavity 25, but still have diaphragm 20. In some embodiments, implant body 8 may have a second cavity 25, but no diaphragm 20. In such embodiments, other means such as, and without limitation, sensors that extend to the measuring site can be used to detect physiological parameters. Further still, some embodiments have neither second internal cavity 25 nor diaphragm 20.

In some embodiments, sensors 22 can be disposed outside of implant body 8 within the implanted environment and can be connected to the internal electronic 28 of implant 2 through hermetic feedthrough 24. In some of these embodiments, sensors 22 can be attached directly on the external face of the hermetic feedthrough 24 and can be either coupled or not coupled with a pressure conduction catheter 12. In some of these embodiments, sensors 22 can be positioned directly at the region targeted for measurement and connected via cables, wires, or leads to the external face of the hermetic feedthrough 24. In some cases, these cables, wires, or leads can extend into conduction catheter 12.

In some embodiments, physiological pressure can be measured by detecting deflection of diaphragm 20 when an external pressure is experienced against a reference pressure within second internal cavity 25. Diaphragm deflection (e.g., deflection of diaphragm 20) can be detected by different means. One such means can be measuring the time of flight for optical, electromagnetic, sonic, and/or other wave to bounce back from the diaphragm 20 to an emitter. Another means can be to measure diaphragm displacement by detecting changes in inductance or capacitance, using a linear variable displacement transformer, or Hall Effect. Diaphragm deflection can also be detected and measured by bonding an array of strain gauges 22 to diaphragm 20 in a quarter, half, or full Wheatstone bridge configuration. A person having ordinary skill the art should appreciate that any number of sensors may be used. An advantage of embodiments described in this disclosure is that the embodiments can enable off-the-shelf sensors to be used as they can be included in an implant that can have a controlled microenvironment and can measure additional physiological parameter that can affect measurements (e.g., measuring temperature as well as pressure).

In some embodiments, sensors 22 in second internal cavity 25 can measure the temperature of diaphragm 20, strain gauge 22, other components of implant 2, or a combination thereof. In some embodiments, there can be at least one temperature sensor and at least one pressure sensor. In some embodiments, there can be no temperature sensor. In some cases, pressure measurements can be susceptible to temperature-induced drift. For example, temperature changes can cause expansion and contraction of diaphragm 20, gauges 22, implant body 8, hermetic feedthrough 24, and gas within internal cavities 16, 25, which can in turn cause changes in strain experienced by the strain gauges that are not related to pressure phenomena. Other components of implant 2 can also be susceptible to physical, chemical, performance, or other changes due to temperature. Therefore, it can be advantageous to measure component temperatures to enable compensation for temperature-induced drift of physiological measurements. Temperature compensation can improve accuracy of physiological parameter measurements. Among other advantages, component temperature can also be used as a means of diagnosing the system.

As implant 2 components can expand and contract with temperature changes. The pressure and volume of internal cavities 16, 25 can also change. In some embodiments, implant 2 can be constructed with materials that have matching or similar coefficients of thermal expansion, which can improve the predictability, stability and linearity of implant 2's structural response to temperature change. This matching can be desirable if the pressure within either or both of the internal cavities 16, 25 are used as reference pressures for pressure measurements (e.g., ICP) since structural changes affect internal pressures and volumes. As illustrated in FIG. 5B, second internal cavity 25, which serves as a reference pressure for pressure responsive diaphragm 20, can be first sealed by hermetic feedthrough 24 and secondarily sealed by cap 10. This can provide increased protection against leakage of the reference pressure. More stable, predictable, and linear reference pressures can allow for better pressure measurement accuracy.

In some embodiments, pressure responsive diaphragm 20 can be constructed from robust materials that have higher resistance to fatigue. For example, in some embodiments, diaphragm 20 can be fabricated with titanium instead of plastic; the physical properties of metal can be less susceptible to fatigue from repetitive movements associated with diaphragm deflection than those of plastics and can exhibit better drift stability. In some embodiments, pressure diaphragm 20 can be constructed from materials that are more hydrophobic, like titanium. Diaphragms made from hydrophobic material can reduce fluid impregnation and absorption of the diaphragms while implanted, thereby maintaining more consistent physical responses to pressure and more drift stability. This can generally be in contrast to diaphragms made from less hydrophobic or more hydrophilic materials—such as plastics and silicone—that can absorb or become impregnated with fluid, resulting in increased measurement drift. In some embodiments, pressure diaphragm 20 can be constructed from materials with lower permeability to reduce liquid or gas exchange across diaphragm 20 to reference pressure chamber 25 and thereby increase drift stability.

In some embodiments, diaphragm 20 can be constructed and then welded and/or otherwise attached to implant body 8. In other embodiments, diaphragm 20 can be integrated into implant body 8. In some cases, such integration can form a unibody construction between implant body 8 and diaphragm 20. For example, and without limitation, implant body 8 and diaphragm 20 can be constructed from a single piece of material (e.g., titanium). Such a unibody construction may be desirable in order to eliminate points of stress/strain and/or weakness introduced by joints. Moreover, a unibody construction may allow for a thinner and/or smaller diaphragm to be used in the implant as desired because diaphragm 20 would not be separately attached to implant body 8. For example, and without limitation, advantageously, diaphragm 20 can be constructed without extra material or thickness for attaching (e.g., welding) to implant body 8 when diaphragm 20 and implant body 8 are unibody.

Furthermore, to measure small changes in physiological pressure—such as ICP—it can be desirable for diaphragm materials to be sufficiently elastic in order to exhibit a detectable degree of deflection. Such a characteristic can be taken into account with other factors, such as adequate robustness, hydrophobicity, and permeability. In some embodiments, diaphragm 20 can be constructed from a robust, hydrophobic, and negligibly permeable material such as titanium. In some cases, a titanium diaphragm 20 can be either very thin or large enough in surface area for a given thickness in order to exhibit sufficiently detectible deflection and sensitivity to intracranial pressures. In some cases, if diaphragm 20 is made from materials usually considered impermeable, making diaphragm 20 too thin can increase the permeability of diaphragm 20 to a level that is no longer negligible. As such, a thinner diaphragm can be desirable if it maintains adequate pressure sensitivity. However, in some cases, a thicker diaphragm 20 can exhibit increased robustness and resistance to fatigue, decreased susceptibility to noise and artifacts, and increased ease of manufacture. Therefore, in some embodiments, if a thicker diaphragm is desirable, in order to make diaphragm 20 thick enough while maintaining pressure sensitivity, the surface area of diaphragm 20 can be enlarged. In some embodiments, diaphragm 20 can comprise a titanium diaphragm made from Grade 5 titanium having a diameter of about 4 millimeters and a thickness of about 0.08 millimeters.

In some embodiments, a diaphragm 20 with a large diameter can cause the implant to be more invasive when implanted into tissue. In such cases, it can be desirable to position implant body 8 and the larger diaphragm 20 in a more superficial and less invasive location—such as outside of the skull or even the superficial of the skin—and to use a smaller pressure conduction catheter 12 to couple the diaphragm 20 to the region targeted for measurement.

The uniformity of diaphragm 20 can be related to the predictability, stability, linearity, accuracy and precision of pressure measurement. One reason for this is that models used to design as well as to calibrate diaphragms sometimes assume an ideally uniform diaphragm. Therefore, a more uniform diaphragm can perform more similarly to the models and calibrations assuming uniformity. Uniformity includes consistency in molecular structure, flatness of the diaphragm, consistency of diaphragm thickness, roughness of the diaphragm surfaces, parallelity of opposing diaphragm faces and so forth. Some methods to fabricate diaphragm 20 with high uniformity can include fabricating diaphragm 20 and the surrounding structure, such as implant body 8, out of a single piece of substrate. The assembly (e.g., including diaphragm 20 and implant body 8) can be fabricated in a single operation in a unibody fashion instead of joining separate components, which can enable greater uniformity. Furthermore, such methods can use fewer operations to fabricate the diaphragm assembly, which can lend to better conformity among fabricated diaphragm assemblies. Better conformity can enable better adherence to calibration models and intended performance.

In some embodiments, diaphragm 20 can be machined into implant body 8 by milling both sides of diaphragm 20 either sequentially or simultaneously to create a more uniform surface. In other embodiments, diaphragm 20 can first be fabricated and then affixed to the surrounding structure. In some cases, diaphragms constructed in this way can be less uniform. For example, and without limitation, a diaphragm can be first cut from a thin film of titanium, and then welded continuously along the periphery to the surrounding structure. In this example, welding can cause structural irregularity around the periphery of the diaphragm, which can make the diaphragm's response to pressure less predictable.

In some embodiments, diaphragm 20 can be fabricated with high uniformity by etching the diaphragm surfaces either after machining or in place of machining. Etching can be desirable to decrease the surface roughness of the diaphragms as compared to machining alone. Etching can also be desirable to produce diaphragms with more even thickness across their surfaces as compared with machining alone. For example, and without limitation, when thin diaphragms are being machined, they can deflect away from the machining tool bit more at the center than at the peripheries, resulting in a diaphragm that can be convex on one or both sides. In some cases, if such a convex shape is not desirable, methods can be performed where the diaphragms are not milled to the desired thickness. Rather, the milling operations can stop when the diaphragms are still thicker than ultimately desired and are significantly more rigid. Since the diaphragms can be thicker and more rigid at that thickness, the diaphragms can deflect significantly less away from the machining bit. This reduction in deflection can result in diaphragms that are thicker, but less convex and therefore flatter. Such thicker, flatter diaphragms can then be etched until the diaphragms reach the desired thickness. Since etching removes material uniformly across a surface, etching can result in much flatter diaphragm surfaces as compared to diaphragms that are only machined. Flatter diaphragm surfaces can ultimately lend to better predictability, stability and consistency of diaphragm responses to changes in pressure. Etching can be accomplished by dry etching or wet etching methods. Dry etching methods can comprise bombarding a substrate with ions or particles to etch out a pattern. Wet etching methods can comprise the use of chemicals to etch a pattern defined by a mask on a substrate. Wet etchants include acids and bases.

Figure 6:
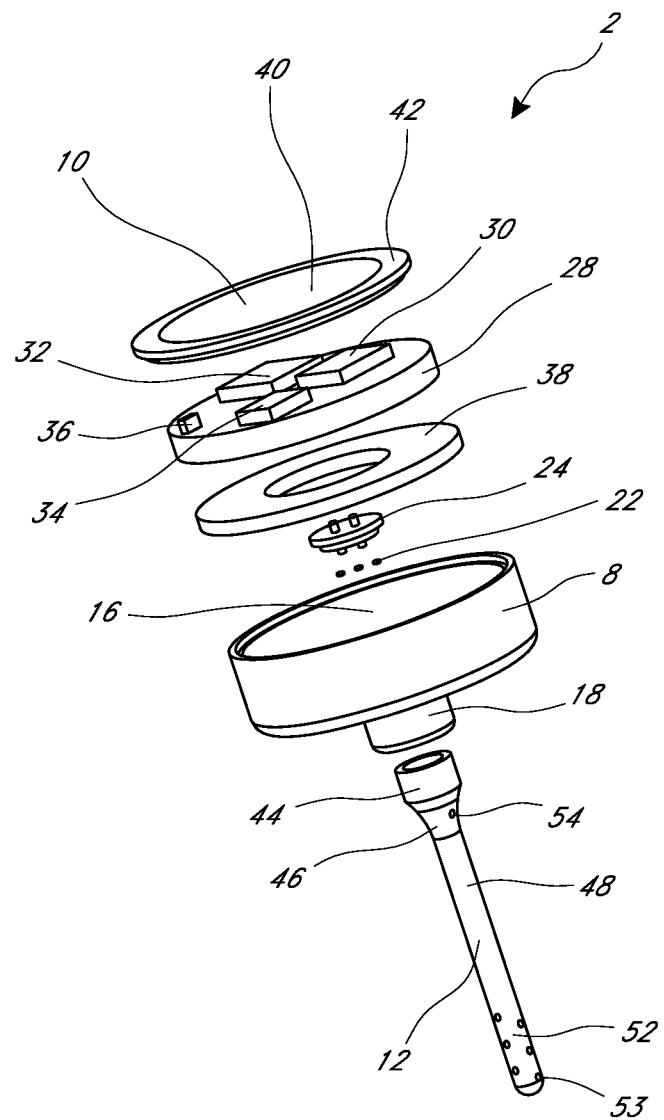
FIG. 6 illustrates an exploded slanted view of the example implant illustrated in FIG. 4.

FIG. 6 illustrates an exploded slanted view of the example implant illustrated in FIG. 4. Pressure conduction catheter 12 can conduct static or dynamic pressure phenomena from distal end 52 to proximal end 44, where it couples to implant body 8 and pressure diaphragm 20. Catheter 12 can be coupled to implant body 8 using mechanical force, such as tension or compression, adhesives, locking pins, other attachment methods, or combinations thereof. The catheter 12 includes a transitional region 46 where the outer diameter of catheter 12 becomes smaller, enabling less invasive insertion through the skull and brain tissue. Dampening of the conducted pressure phenomena can be allowed, caused, or prevented by configuring the rigidity of the walls of catheter 12 through different structural designs or chemical compositions. The length of the catheter 12 from the distal surface of the body 8 to distal end 52 can be generally within the range from about 0.5 cm to about 10 cm. In some example embodiments, it can be within the range of from about 1 cm to about 8 cm. Also, in some example embodiments, it can be about 1.5 cm. The diameter of catheter 12 can be generally within the range from about 1 mm to about 5 mm. In some example embodiments, it can be within the range of from about 1 mm to about 2.5 mm. In some example embodiments, it can be about 2 mm. The thickness of the wall of catheter 12 can be generally within the range from about 0.2 mm to about 1 mm. In some example embodiments, it can be within the range of from about 0.3 mm to about 0.8 mm. Also, in some example embodiments, it can be about 0.5 mm.

In some embodiments, pressure can be conducted from a measured region of tissue through ports 53, 55 (which can be perforations, apertures, windows, holes, punctures, etc.) at distal end 52 of catheter 12 through the gas, liquid, gel or solid medium within the inner lumen of the catheter 12 up to diaphragm 20. For example, a pressure conduction catheter 12 that is 1.5 cm in length can allow measurements of the parenchymal region of the brain, and a longer catheter 12 can allow measurements of the ventricular region of the brain. Dampening can be allowed, caused, or prevented by configuring the rigidity of said medium through different combinations of media, structural designs, chemical compositions, or combinations thereof. During the course of implantation, catheter 12, if originally filled with a medium or media either during manufacture or at the implantation site, can become partially or fully displaced with intracranial fluid. The fluid can enter due to catheter 12 insertion, capillary action along the inner surface of catheter 12, rise in intracranial pressure, or other reasons. In some cases, if catheter 12 is initially filled with a medium or media, invasion of intracranial fluid or gas can trap and possibly compress a volume of the media in proximal end 44 of catheter 12. The use of the medium or media can be desirable if direct contact between intracranial fluid or intracranial gas is not desired and the original media serves as a barrier. One example, of why direct contact between the diaphragm and intracranial fluid/gas may not be desirable is that intracranial fluid/gas can cause clotting or tissue growth on the pressure diaphragm 20 if it is in direct contact. This growth can result in pressure measurement inaccuracies or drift. If a volume of trapped original media is not desired within catheter 12 during and after implantation, a vent hole 54 can be incorporated near proximal end 44 of catheter 12. This vent hole 54 can allow the trapped original media to exit if catheter 12 is invaded by intracranial fluid or gas from distal end 52. The size and shape of vent hole 54 can be configured to allow, cause, or prevent pressure conduction dampening. Allowing catheter 12 to fill with intracranial fluid or gas can compensate for intracranial volume displacement caused by the original media in catheter 12, thereby avoiding further rises in intracranial pressure in subjects who can already have elevated pressure.

In some embodiments, configuring the length of catheter 12 can enable variability of measurement location. In some embodiments, implant 2 can be provided with a catheter 12 that is longer than desired. The user can trim the length of catheter 12 so that distal end 52 terminates at the desired measurement depth if implant 2 is inserted into the subject. In these embodiments, configuring the length of an intracranial pressure monitoring implant can enable the user to determine if pressure is monitored at the epidural, subdural, parenchymal, or ventricular depth. In some embodiments, implant 2 can be provided with multiple catheters with varying lengths, shapes, sizes and/or geometries that can be selected and attached to implant body 8 to determine monitoring modality.

In some embodiments, the effects of occlusion at distal end 52 of catheter 12 can be reduced and/or prevented with additional ports (e.g., port 53) along the side wall of catheter 12. Multiple ports can be made along the catheter to mitigate the effects of occlusion—due to, for example and without limitation, clotting, tissue growth, tissue contact, coverage, and/or other causes—of some of the ports; if some of the ports become occluded, the presence of other ports can allow continued pressure communication into catheter 12. Radial ports in catheter 12, as illustrated in FIG. 6, can mitigate the effects of occlusion at axial catheter opening 55 that can occur during catheter insertion into tissue. Multiple ports radially around catheter 12 can allow, if a directional force (e.g., gravity) is causing tissue contact to block ports on one side of catheter 12, for the ports on the opposite side to be still able to conduct pressure into catheter 12. There can also be cases where multi-directional forces, like brain edema, can cause tissue to contact and block ports in all directions. To address these cases, some embodiments of the invention can include grooves and channels on the outer surface of catheter 12 that extend from the ports. These grooves and channels can prevent blockage and provide conduits for pressure communication into catheter 12 even if there is tissue pressing against catheter 12. In some embodiments, a barrier (e.g., barrier 813 illustrated in FIG. 8), such as a sheath, balloon, and/or covering, can be positioned along catheter 12. The barrier can be positioned such that it covers some of and/or all of the ports, and can prevent blockage of some of and/or all of the ports.

In some embodiments, different perforation patterns along catheter 12 can be used to configure the pressure monitoring region. For example, and without limitation, facing the ports in a single direction can enable directional pressure measurement. Having ports toward proximal end 44 with no distal ports can result in a shallower region of pressure measurements while ports toward distal end 52 can result in a deeper region of pressure measurement. Having tighter grouping of ports can yield a smaller region of pressure measurement, and more spread-out grouping of ports can yield a larger region of pressure measurement. Having ports along the entire length of pressure conduction catheter 12 can enable measurement across the range of depths in the brain, representing a more global intracranial pressure measurement. In contrast, some conventional intracranial pressure monitors can only measure local, regional pressures that are not representative of the pressure experienced by the organ globally. Such regional pressures can be a consequence of the compartmentalization of brain tissue. In some embodiments, if pressure conduction catheter 12 is perforated along its entire length, the pressure experienced by pressure diaphragm 20 can be the sum of pressure at all depths of the brain that the catheter traverses. This can yield a more global measurement of intracranial pressure. Again, any of the above described perforation patterns can be used in conjunction with a barrier (e.g., barrier 813 illustrated in FIG. 8), such as a sheath, balloon, and/or covering, that can be positioned such that it covers some of and/or all of the ports, and can prevent blockage of some of and/or all of ports. In some embodiments, the barrier can be configured to not interfere with pressure measurements as will later be described. Though, even if the barrier does collapse on catheter 12 in some embodiments, pressure measurements can still be taken. Similarly, even if the barrier expands so that it is in tension (e.g., its surface is in tension), measurements can still be taken.

In some embodiments, instead of pressure sensing diaphragm 20 being integrated with implant body 8, the pressure sensor, or any other sensor, can be disposed along or at the distal end of a probe. The probe can attach to implant body 8 in a manner substantially similar to the way pressure conduction catheter 12 can be attached. Diaphragm 20 on the implant body 8 can be either perforated, or not perforated at all, and the leads for the sensors can be attached through the hermetic feedthrough 24 to the internal electronics 28. The probe can serve as mechanical support for the leads, electrical insulation, thermal insulation, liquid barrier, gas barrier, and the like or any combination thereof. The sensor or multiple sensors can be disposed in varying patterns along the probe or at the distal end of catheter 12.

These embodiments can also be configurable. Multiple probes with various lengths and different types of sensors can be provided to the user for selection and attachment to implant body 8 depending on the desired usage. The attachment of sensor leads to hermetic feedthrough 24 can be press fit or some other similar method that enables connection of sensor leads to a feed though. Some examples of sensors that could be press fitted are miniature MEMS pressure sensors, tissue oxygenation sensors, temperature sensors, flow sensors, and the like. The use of a sensor probe can be used in conjunction with a system that incorporates an integrated pressure diaphragm with or without a pressure conduction catheter. For example, and without limitation, catheter 12 can serve as the probe and the sensor leads can be disposed directly within catheter 12. In this example, if there is gas or fluid along the catheter alongside the sensor leads, catheter 12 can still conduct pressure to diaphragm 20. In some embodiments, the probe that houses the sensors leads can be disposed within pressure conduction catheter 12. In some embodiments, the probe can extend separately from implant body 8 than catheter 12. In these embodiments, a second hermetic feedthrough (or more hermetic feedthroughs) can be incorporated into implant body 8 to enable sensor lead connection to internal electronics 28 of implant 2 in a fashion that does not interfere with the functioning of diaphragm 20.

In some embodiments, parameters other than ICP can be measured either in substitution of or in combination with ICP. Examples of other parameters include, but are not limited to, tissue oxygenation, temperature, time, fluid flow, position, radiation exposure, and others. Sensing means for these parameters can be similarly incorporated into the body of implant 8, attached along a probe 12, attached to internal electronics assembly 28, or a combination thereof.

Implant 2 can incorporate electronics assembly 28, which can include support electronics for sensors, electronics to carry out analog-to-digital computing, and electronics to enable wireless communication. In some embodiments, electronics assembly 28 is wholly or partially disposed on one or multiple printed circuit boards (e.g., PCBAs). In some embodiments, electronics assembly 28 is comprised of analog circuitry for detecting, processing, and transmitting sensor data. In some embodiments, electronics assembly 28 can comprised digital circuitry with optional inclusion of analog support circuitry. For example, electronics assembly 28 can include one, or multiple, analog-to-digital converter modules 30, which convert analog sensor output to a digital representation. Analog-to-digital converter modules 30 can be standalone components of the circuitry, integrated into sensor units 22, or integrated into microcontroller processor modules 32, which may include a controller, processor, CPU, microprocessor, application-specific integrated circuit ("ASIC"), programmable logic devices ("PLD"), field-programmable gate arrays ("FPGA"), etc. Processor modules 32 can be configured to perform one or more of: processing inputs received from sensors, filtering noise, amplifying data signals, storing data, and the like. Amplification of data signals can also occur within sensor modules 22, as a standalone portion of the circuitry, or not occur at all. In some embodiments, components typically used to amplify sensor signals are omitted from the circuitry to conserve space in implant body 8 and enable a smaller implant 2. In some cases, if desired, a higher bit analog-to-digital converter 30 can be used to achieve the same resolution of parameter measurement as the resolution provided by a lower bit analog-to-digital converter 30 used in conjunction with an amplifier. Another component in electronics assembly 28 can be telemetry circuitry 34, including a wireless communication antenna 36 that enables wireless communication. In addition to enabling wireless communication, telemetry circuitry 34 can include circuitry to encode data or communications, tag transmitted data with additional information like time stamps, pre-filter, establish wireless pairing, provide communication security, etc. Telemetry circuitry 34 can be implemented as a standalone module of electronics assembly 28 or can be incorporate wholly or in part within processing module 32. In some embodiments, telemetry circuitry 34 implements Bluetooth low energy protocol for wireless communication with a remote device.

Electronics assembly 28 can be powered by a power source. In some embodiments, the power source can be a battery housed within implant body 8 or, alternatively, housed outside of implant body 8 and connected via a feedthrough into electronics assembly 28 within implant body 8. In some embodiments, the power source can be a battery that is single use. In some embodiments, the power source can be a rechargeable battery that can be recharged either by conventional wired methods through a hermetic feedthrough into the implant housing or through wireless power transfer, such as inductive power transfer, optical power transfer, motion energy capture, heat capture, light capture, or the like. In some embodiments, the power source can be a fuel cell, solar cell, or means for mechanical energy storage. In some embodiments, the power source can be a capacitor that is charged wirelessly through inductive power transfer.

In some embodiments, the packaging of a wireless power-transmitting unit and a wireless power-receiving unit for transport to the deployment site can be such that the units are aligned for optimal wireless power transfer inside the package. In some embodiments where wireless power transfer is achieved through inductive coupling, the primary coil (which can send energy) can be packaged in such a way with the secondary coil (which can receive energy) that the coils can be physically aligned for maximum power transfer efficiency. The desired alignment of the primary and secondary coils used in inductive power transfer can be found by ways known by those with ordinary skill in the art. For example, and without limitation, the desired alignment can be based at least in part on maximizing the coupling factor between the power-transmitting unit and the power-receiving unit. In some embodiments, where wireless power transfer can be achieved through optical coupling, the optical source is packaged with the optical receiver in such a way that they are aligned with a clear line-of-sight for maximum power transfer efficiency. In some embodiments, when power-transmitting and power-receiving units are packaged, transported, stored and opened in such configurations at the point of deployment, the wireless power transfer functionality can be engaged, turned on, and/or started without disturbing their pre-packaged alignment. If the wireless powering is successful, the method can verify functionality of the power transfer feature. If the wireless powering is unsuccessful, the method can verify non-functionality of the power transfer feature since physical alignment can already be such that there should be maximum power transfer efficiency. In some embodiments, the system can record the wireless power transfer efficiency experienced during this ideal alignment and use that as the reference for judging wireless power performance after deployment and during operation.

In some embodiments, disclosed methods comprise packaging a power sending unit or a multitude of power sending units with a power receiving unit or a multitude of power receiving units in a packaging container in a physical configuration for a desired wireless power transfer efficiency (e.g., a maximum power transfer efficiency), opening the package and engaging the units, starting or turning on the power transfer functionality of the power sending unit(s) and the power receiving unit(s), and then verifying the power transfer.

These methods can be advantageous over other methods of checking for wireless power functionality and performance prior to deployment because the methods can test power transfer efficiency and functionality while the sending and receiving coils are in a physical configuration for maximum power efficiency. Testing wireless power functionality using other methods, such as holding the power-transmitting and power-receiving units in position manually, can be susceptible to inconsistency, imprecision, human error and other issues. This susceptibility can arise because poor wireless power functionality can result from poor physical alignment by user instead of inherent feature functionality.

In some embodiments, the power sending unit(s) and the power receiving unit(s) can be programmed during manufacture as a pair. Such programming may be desirable to allow the units to pair without pairing protocols during system deployment. In some cases, eliminating pairing protocols during system deployment may increase data security by eliminating the possibility of breach during the pairing protocols.

In some embodiments, the power source can be power-receiving coil 38. Power-receiving coil 38 is illustrated as a ring FIG. 6, but other geometries can be used for inductive power reception. In some embodiments, implant 2 can be powered transiently and can operate while in the presence of wirelessly transmitted energy. For example and without limitation, an advantage of a transient wireless power system can be the relative simplicity of the system as well as simplicity of operation. In some cases, simpler systems can have fewer failure modes and less training burden for new operators. Another advantage of transient wireless power is that the absence of stored energy reduces the safety risk of the system. For example, batteries can leak, overheat, and malfunction causing injury to the patient.

In some embodiments, implant 2 can enable passage of wireless communications and wireless power transmissions into and out of the implant internal cavity 16. In some cases, if implant cap 10 and implant body 8 are both made from conductive material, they can act as a Faraday's cage and block or attenuate electromagnetic signals into and out of internal cavity 16. Therefore, it can be desirable to incorporate a portion made from materials such as glass or ceramic that can permit passage of wireless transmissions into the implant cap 10. In some embodiments, this portion is a radiofrequency window 40 that forms a part of the implant cap 10 and allows passage of radiofrequency signals. In some cases, if wireless transmission is implemented optically, the wirelessly traversable region can serve as an optical window.

In some embodiments, the entire cap can be constructed from a wirelessly traversable material and services as a window. In some embodiments, the process for hermetically sealing implant cap 10 (e.g., made with certain materials like ceramic or glass) to implant body 8 (e.g., made from certain materials like titanium or other metals) can cause high temperatures to be applied to the entire implant assembly. Such processes include brazing and compression sealing processes. Exposing internal components (e.g., electronics assembly 28, power-receiving coil 38, and/or sensor modules 22) within implant body 8 to these high temperatures can damage or impact the performance or functionality of these internal components. Thus, in some embodiments, window 40 can be first brazed or compression sealed to rim 42 to form implant cap 10. The assembled implant cap 10 can then be hermetically sealed to implant body 8 with a process that minimizes and/or reduces global heating of implant 2. In some embodiments, window 40 can be a ceramic disc that is brazed to a titanium ring 42 to form implant cap 10. Then, implant cap 10 can be laser welded to implant body 8. In some cases, laser welding may only generate high temperatures at the welding site and may not cause global heating of the work piece. Moreover, the work piece can be coupled to a heat-sink to ensure damaging levels of heat are not conducted from the welding site to other areas of the work piece. In these ways, some embodiments enable incorporation of hermetically sealed radiofrequency window 40 into implants 2 that contain heat-sensitive internal components.

In some embodiments, wireless power can be transmitted at 13.56 MHz, although other frequencies can be used. For example, and without limitation, implants can use any frequency within the range 100 kHz to 15 MHz depending on factors such as implant size, tissue type, and/or depth of implantation. For the implant, smaller components can be used to receive power at higher frequencies (e.g., closer to 15 MHz) than lower frequencies (e.g., closer to 100 kHz). However, higher frequency power signals can have worse tissue penetration than lower frequency power signals because higher frequency power signals can be more likely to get trapped in tissue and heat up that tissue. Accordingly, using lower frequency power signals may be desirable to power implants positioned deeper in the tissue of a patient. A person having ordinary skill in the art should appreciate that selecting a particular frequency in the aforementioned range may be done by balancing the aforementioned factors.

In some embodiments, a frequency of 13.56 MHz can be desirable because the frequency is an ISM band that can balance the tissue penetration characteristics and the size of the required supporting electronics components to yield sufficient power transfer quality while minimizing component size, and therefor invasiveness, of the implant. Another factor may be frequency density and/or interference of other operating devices. Moreover, 13.56 MHz, which is a frequency at the higher end of the 100 kHz to 15 MHz range, may be desirable because implants in the skull are close to the tissue surface and power would not need to penetrate deep into tissue. In some embodiments, wireless data can be transmitted at 2.4 GHz, although other frequencies can be used. A frequency of 2.4 GHz can be a desirable frequency because it is an ISM band. In some embodiments, the wireless power transmission frequency and the wireless communication frequency can be spread apart on the frequency spectrum to minimize interference between the two transmissions. A person having ordinary skill in the art should appreciate that there are many frequencies that can be used for transmission. For example and without limitation, data transmission can use any frequency used in the range of telecommunications, including frequencies in the range 698 MHz to 2.8 GHz. A particular frequency can be chosen based on any of the characteristics described above with respect to power signals.

In some embodiments, the data antenna and the power antenna may be integrated into a circuit that transmits and receives both data and power. For example, and without limitation, the power signal may be modulated to send data. However, in some embodiments, it may be desirable to have separate systems (e.g., components) for power and for data. Such separation may advantageously allow increased flexibility in design considerations, including the frequencies used for power and/or data transmission. In some cases, having separate systems allows for higher frequency data signals, that may allow for higher transfer rates of data than a single, integrated system. Similarly, having separate systems can also provide for higher fidelity data signals through the use of a distinct data channel. Moreover, using separate systems can allow for component modularity of the power and/or data systems, where either system can be changed, upgraded, and/or replaced. For example, and without limitation, the wireless power system may be exchanged with a battery. Also, the data system may be upgraded with advances and/or changes in communication protocols.

Figure 7:
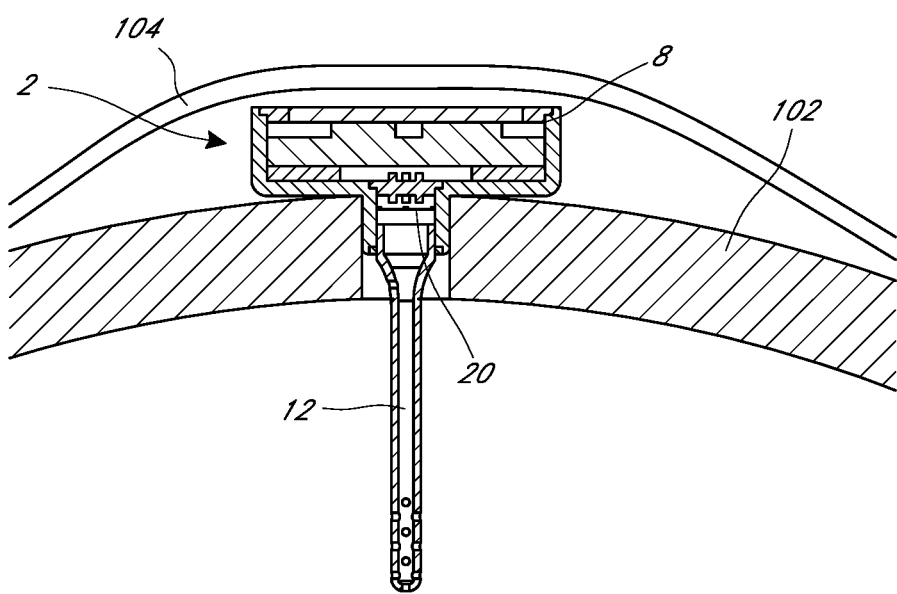
FIG. 7 illustrates a cross section view of the example implant illustrated in FIG. 4 implanted in a skull.

FIG. 7 illustrates a cross section view of the example implant illustrated in FIG. 4 implanted in a skull. Implant body 8 with integrated pressure diaphragms 20 can be implanted on the outer table of skull 102 but underneath skin 104. Pressure conduction catheter 12 can be coupled to implant body 8 and extend through a cranial burr hole into the epidural, subdural, parenchymal, or ventricular space. In some other embodiments, implant body 8 can be secured to the outside of the scalp and catheter 12 can extend (e.g., in an axial direction) through an incision on the scalp, though a burr hole, and to the targeted measurement site. This construction can enable the use of larger, thicker pressure diaphragm designs, which can be desirable for accuracy, drift stability, and sensitivity, and can be less invasive than implanting larger diaphragms directly into the cranium.

In some embodiments, portions of implant 2 that extend into the brain (e.g., catheter 12 and/or any sensors that may extend through the catheter and/or outside of catheter 12) may not comprise metals and/or ferrous materials. Such may be advantageous in order to make implant 2 MRI safe because metals and/or ferrous materials may have responses to MRI signals. Such response can include heating tissue and/or movement. Another advantage of not using such metals and/or ferrous materials is to provide thermal and/or electrical insulation from implant body 8 so that any heat and/or electricity generated or received on implant body 8 may not conduct to the brain tissue.

Figure 8:
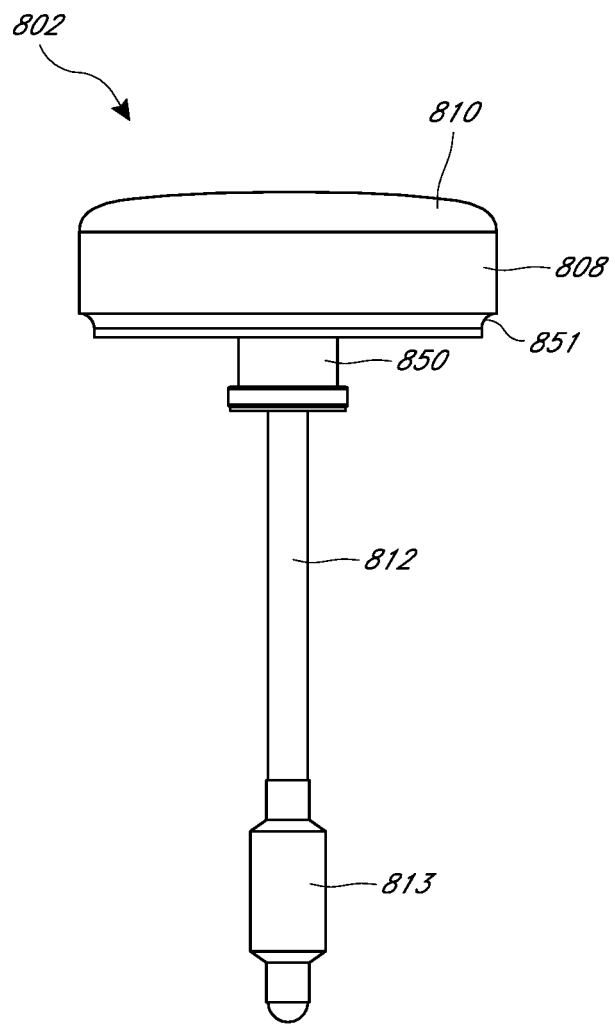
FIG. 8 illustrates an example implant having a single chamber housing the electronics and holding a reference pressure.

FIG. 8 illustrates an example implant having a single chamber housing the electronics and holding a reference pressure. The example implant may incorporate, or not incorporate, any of the features described in this disclosure with reference to the other figures. Encapsulation 810 can be placed on an end of implant body 808. For example, encapsulation 810 can be placed at a surface of implant body 808 distal to a patient's skull. Encapsulation 810 can house a data antenna and power coil (e.g., data antenna 837 and/or power coil 838 illustrated in FIG. 9). In some cases, because a metal casing can act as a Faraday cage, which can cause losses in transmission efficiency and/or interference with other electronics, it may be desirable for encapsulation 810 to comprise non-conducting materials, such as (and without limitation) silicone, epoxy, glass, ceramic, and/or plastic. In this way, data antenna 837 and power coil 838 can be encapsulated and protected/insulated from the patient and other electronics of implant 802. For example, encapsulation 810 can protect the patient tissue from coming into contact with potentially bio-incompatible materials inside. Encapsulation 810 can also protect the internal electronics from short circuiting and/or corroding due to fluid and gas ingress in the implanted setting.

For example, and without limitation, encapsulation 810 can be a preformed lid that is glued and/or epoxied onto implant body 808. The lid can be made from a silicone mold that can be configured to fit over implant body 808. The mold can then be filled with epoxy to cast it into the appropriate shape. In some cases, outgas from the epoxy can cause bubbles to form in the epoxy. It may be desirable to prevent such bubbles from forming. For example, and without limitation, the following methods can be used alone or in combination to remove bubbles. In some cases, the mold and/or epoxy can be vibrated during curing. In some cases, a relative vacuum can be used to pull the bubbles out of the epoxy. In some cases, the epoxy can be cured under high pressure to prevent bubbles from forming. In some embodiments, encapsulation 810 can be a potting that is cast and formed directly on the implant. In some cases, encapsulation 810 can be cast to a lid assembly first before attaching encapsulation 810 to the rest of the implant body.

Implant body 808 can comprise titanium and/or any other biocompatible material used to enclose electronics within a hermetic seal. Implant body 808 can interface with pressure conduction catheter 812 at its proximal end through a catheter junction (e.g., catheter junction 811 illustrated in FIG. 9), which can be machined from PEEK and/or other biocompatible materials. In some cases, the catheter junction can be injection molded instead of machined.

Catheter 812 can comprise a urethane catheter. In some cases, there can be no electronics or wires inside of pressure conduction catheter 812. Catheter 812 can provide a fluid or gas column from the target measurement area to the sensing diaphragm (e.g., diaphragm 820 illustrated in FIG. 10B). Neck 850 can interphase implant body 808 with catheter 812.

Barrier 813, which can be a sheath, balloon, and/or other covering, can be positioned such that it covers some of and/or all of the ports (e.g., port 853 illustrated in FIG. 9), which can include perforations, apertures, windows, holes, punctures, etc., and can prevent blockage of some of and/or all of the ports. In some embodiments, barrier 813 can be a thin-walled sac configured to protect ports from occlusion while implanted. In some embodiments, for example and without limitation, barrier 813 can be coated in a coating, gel, chemical, and/or any substance through a treatment processing such as dipping. Occlusion can result from debris clogging the ports and/or the inner lumen of catheter 812. There can also be cellular, tissue, protein, blood clot, etc. built up to occlude the ports or catheter. An advantage of some embodiments is that even if there is growth or clotting around a portion of barrier 813, there can still be reliable pressure conduction into and up catheter 812. In some embodiments, barrier 813 can be laser bonded to catheter 812. In some embodiments, barrier 813 can be adhered with glue, epoxy, a solvent bonded to form a chemical fusion, ultrasonic welding, heat welding, etc. In some embodiments, it may be desirable to make the bond between barrier 813 and catheter 812 airtight in order to prevent gas and/or liquid from entering and leaving barrier 813 and/or catheter 812.

In some embodiments, barrier 813 may be inflated (or not inflated) so that it is not in tension. For example, and without limitation, barrier 813 can be a sac of gas and/or fluid used as a pressure conduction medium. Such can be desirable in some cases because a barrier in tension can disadvantageously act as a diaphragm and its pressure responses can change as its environment changes (e.g., changes in temperature), and/or if it uptakes fluids and/or lipids in the implanted setting. In some cases, these responses cause measurement drift. For example, a barrier in tension can disadvantageously experience gas diffusion and permeation across its membrane, which can cause the volume of gas within the barrier (and catheter) to vary based at least in part on environmental factors. In some cases, if the barrier is a balloon comprising of urethane, the balloon can disadvantageously uptake liquid and/or lipids, which can lead to drift by causing the balloon to swell. In contrast, in some embodiments, barrier 813 can comprise relatively impermeable materials to substantially prevent and/or reduce the amount of gas, liquid, and/or lipids that can pass through barrier 813. In some embodiments, barrier 813 can comprise polyethylene, plastic, PEEK, nylon, silicone, etc.

In some cases, a barrier not in tension may not experience some of the aforementioned responses and drift. In some embodiments, in order to create a barrier that is not in tension and does not collapse onto the catheter (e.g., blocking the ports), a number of gas molecules in a predetermined range of molecules can be used to fill the internal catheter and barrier so that the barrier is not in tension (e.g., the barrier having slack) and does not collapse onto the catheter in an operable range (e.g., a predefined operable range of measurement environment conditions, including one or more of ICP, pressure at the barrier, temperature, atmospheric pressure, position/orientation, etc.). Advantageously, by configuring the system so that the barrier neither goes in tension nor collapses on the catheter, the presence of the barrier may not introduce substantial variability (e.g., in the form of drift) to the measurements taken by the implant.

The operable range can comprise all foreseeable conditions experienced by the barrier. In this range, the number of gas molecules in the internal catheter assembly can be set so that the volume of gas sealed inside does not expand or contract with altitude changes, temperature changes, pressure changes, position changes, and/or other changes in environmental conditions to the point of putting the barrier in tension or collapsing it. For example and without limitation, typical atmospheric pressures in the measuring environment can range from 400 mmHg to 900 mmHg. ICP, while dependent on factors such as head position/orientation, atmospheric pressure, temperature, and/or other environmental factors, can typically range from −100 mmHg to 150 mmHg, where many patients will have ICPs between −20 mmHg to 50 mmHg. Accordingly, the pressure at the barrier can range from 300 mmHg to 1050 mmHg. In some cases, ICP is interpreted as cranial pressure minus atmospheric pressure. Temperature at the barrier can typically range from 15 degrees to 40 degrees Celsius. Typical operating temperature can be body temperature (e.g., around 37 degrees Celsius) or can be a hypothermic environment typically in the range of 25 degrees to 35 degrees Celsius. The volume of the catheter and the volume of the barrier (and/or a portion of the barrier that is compressible) can vary by the patient and region of the brain desired to be measured. A person having ordinary skill in the art should appreciate that the operating range can vary as desired, and systems and methods described in this disclosure can be configured to operate in those ranges. The number of gas molecules used to fill the internal catheter and barrier can be found using, at least in part, relationships between the volume, pressure, number of molecules, and temperature. For example and without limitation, the ideal gas law, PV=nRT can be used, where P is the pressure, V is the volume, n is the number of molecules of gas, T is the temperature, and R is the gas constant (e.g., 0.08206 L*atm*mol$^{-1}$K$^{-1}$). In some embodiments, the desired volume of gas can be a volume greater than the static volume of the catheter in operation. This desired volume can represent the volume of gas where the barrier does not collapse onto the catheter. The desired volume of gas can also be less than the combined volume of the catheter and the static geometry of the barrier when it just comes into tension. This desired volume can represent the volume of gas where the barrier is not in tension. Assuming a predetermined range of temperatures and pressures experienced by the catheter in the implant environment, the desired number of molecules can be calculated so that the volume stays within the above-described range where the volume is greater than the static volume of the catheter and smaller than the combined volume of the catheter and the static geometry of the barrier in the operable range. Accordingly, the number of molecules of gas can fall within a range, where any number of molecules in that range can be used. A number of molecules of gas in that range can be put into the combined catheter and barrier construction before the implant is implanted.

In some embodiments, the catheter can be filled with an incompressible fluid or gel that substantially does not expand or contract. For example, and without limitation, such incompressible fluid can comprise 0.9% saline. In some cases, 0.9% saline can prevent diffusion or osmosis by substantially matching the in-vivo ionic concentration. In some cases preventing drift with the aforementioned barrier that is not in tension can be desirable in allowing a broad spectrum of sensors, including any off-the-shelf sensor, to be compatible with embodiments of this disclosure.

In some embodiments, using a barrier may also be advantageous to take measurements over a broad area of the brain. In some patients, the patient's brain can have pockets of different pressures and/or different physiological characteristics than other portions of the brain. In conventional methods of measuring ICP and/or other physiological parameters, if sensors were placed in such a pocket, the measurements taken by the sensors may not be representative of the brain and/or region of the brain as a whole. Using a barrier can allow measurements to be taken across a broader range along the entire surface of the barrier. As discussed in this disclosure, the barrier can have different geometries and/or shapes and/or lengths as desired in order to configure the barrier to span certain segments of the brain for measurement of ICP and/or other physiological parameters.

Figure 9:
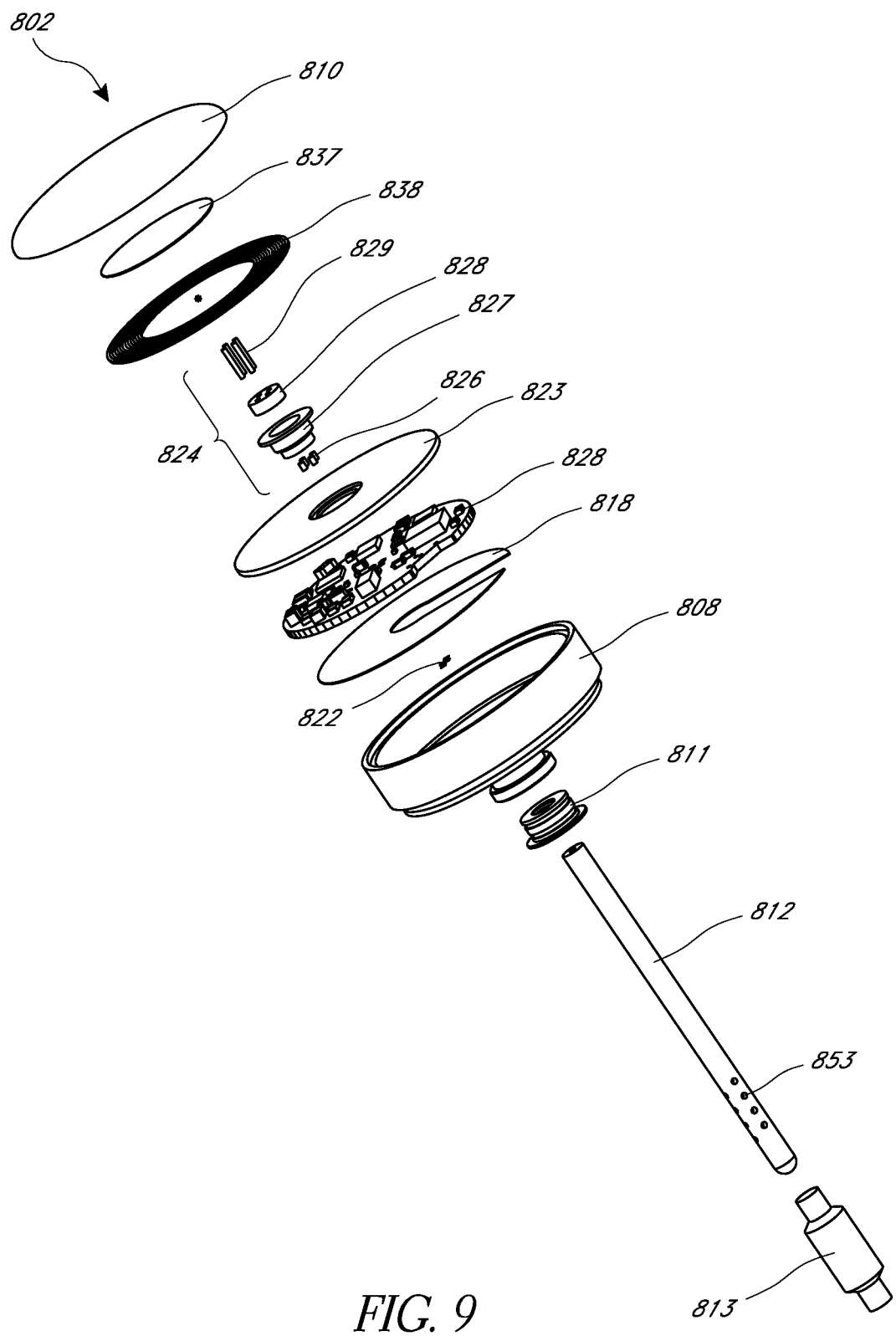
FIG. 9 illustrates an exploded slanted view of the example implant illustrated in FIG. 8.

FIG. 9 illustrates an exploded slanted view of the example implant illustrated in FIG. 8. Data antenna 837 and power coil 838 can operate as any data antenna and power coil described in this disclosure. Data antenna 837 and power coil 838 can be encased in encapsulation 810, and implant lid 823. A separate compartment formed by implant body 808 and implant lid 823 can house electronics and also a reference pressure. This compartment can be hermetically sealed in order to protect the patient from materials within the chamber and to protect the electronics within the chamber from the implanted setting.

Electronics assembly 828 (e.g., a PCBA) can be positioned in the compartment formed by implant body 808 and implant lid 823. Electronics assembly 828 can comprise a processor (e.g., any processor described in this disclosure), memory (e.g., any memory disclosed in this disclosure), and/or other electronics for the functionality of the implant (e.g., any electronics described in this disclosure). Insulating layer 818 can be disposed on the proximal side of electronics assembly 828, between electronics assembly 828 and the wall of implant body 808. Insulating layer 818 can serve to insulate (e.g., as a non-conductor) electronics assembly 828 from implant body 808 and also hold electronics assembly 828 in place. In some cases, insulating layer 818 can be a polyimide double-sided tape.

Figure 10A:
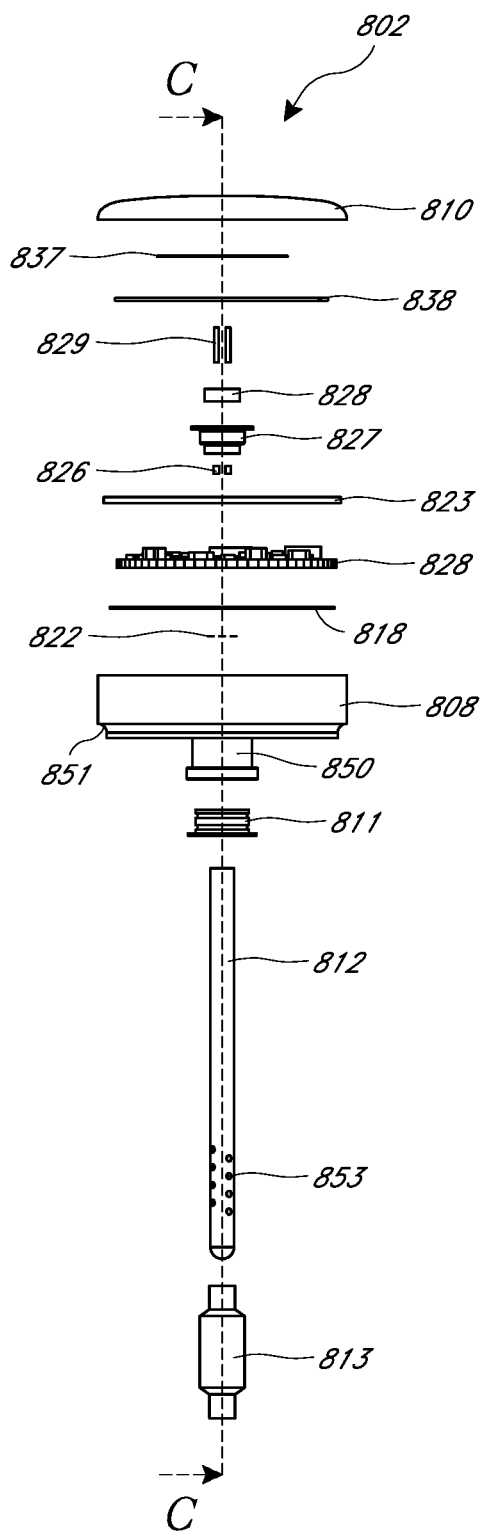
FIG. 10A-B illustrates a front-exploded and cross-sectional view of the example implant illustrated in FIG. 8.
Figure 10B:
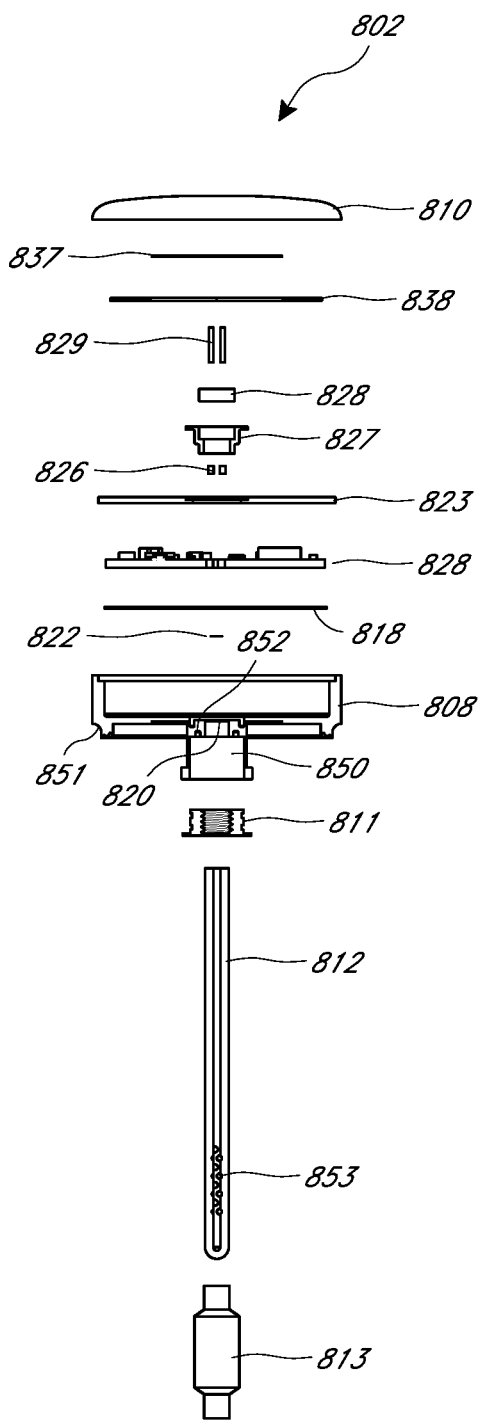

Sensors 822 (e.g., any sensor described in this disclosure) can be positioned on the proximal side of insulating layer 818 to measure, for example and without limitation, the strain on a diaphragm (e.g., diaphragm 820 illustrated on FIG. 10B). Such measurements can be indicative of ICP and/or any other physiological parameter described in this disclosure. Insulating layer 818 can have a hole and/or slit positioned to allow sensors 822 to electrically couple with electronics assembly 828.

Data antenna 837 and power coil 838 can also communicate to electronics assembly 828 and/or any component within the hermetically sealed compartment formed by implant body 808 and implant lid 823 by hermetic feedthrough 824. Hermetic feedthrough 824 can comprise pins 829. In some cases, pins 829 can comprise tantalum, other refractory metals, and/or other biocompatible metals. In some cases, electrical connections to data antenna 837 and power coil 838 can be welded to each of data antenna 837 and power coil 838. Any suitable material can be used for such welding. In some embodiments, tantalum pins can interface hermetic seal 828, which can comprise glass, ceramic, and/or other insulating materials. For example, hermetic seal 828 can be CABAL 12 glass beads. In some cases, each of pins 829 can be inserted axially through holes disposed in hermetic seal 828. These holes can pass through hermetic seal 828, allowing pins 829 to transverse the body of hermetic seal 828. Insulating material can pass axially though header 827, which can comprise titanium and/or any other biocompatible material. In some cases, header 827 can comprise the same material (e.g., titanium) as implant body 808. In some embodiments, where pins 829 comprise refractory metals (e.g., tantalum), soldering pins 829 can be difficult because refractory metals can be resistant to heat. In order to electronically connect the proximal end of these pins 829 to electronics assembly 828, ring electrodes 826 can be laser welded to pins 829 and electronics assembly 828. For example, and without limitation, ring electrodes 826 can comprise a platinum-iridium alloy or other solderable materials suitable for laser welding. In other embodiments, for example and without limitation, where pins 829 comprise other, non-refractory metal materials, ring electrodes 826 may not be used, and pins 829 can be soldered and/or otherwise attached directly to electronics assembly 828.

Catheter 812 can attach to catheter junction 811 by epoxy, press-fit, screw fit, luer lock fitting, and/or any other connection. Catheter junction 811 can also be a single injection molded piece integrated with catheter 812. Catheter junction 811 can further connect to neck 850 by epoxy, press-fit, screw fit, luer lock fitting, and/or any other connection. The inner surface of catheter junction 811 can be threaded. The threads can give greater surface area for epoxy bonding. Moreover, the threads can cast the epoxy to provide a contoured, mechanical fit, which can provide better sealing integrity between catheter junction 811 and catheter 812. Neck 850 can further comprise flanges that allow neck 850 to contact the walls of the burr hole at consistent points. The flanges can also guide and center implant 802 into the center of the burr hole.

FIG. 10A-B illustrates a front-exploded and cross-sectional view of the example implant illustrated in FIG. 8. FIG. 10B is a cross-sectional view along of FIG. 10A along cutline C. Diaphragm 820 can be positioned at the proximal end of implant body 808, and at the distal end of catheter 812. Diaphragm 820 can be a pressure sensing diaphragm, and/or any diaphragm as described in this disclosure. In some cases, Diaphragm 820 can be carried by and/or secured to the proximal end of catheter 812.

A plurality of strain reliefs, such as strain relief 852, can be positioned in the implant body 808 in order to isolate side-loading forces. In some cases, when implant 802 is placed into a burr hole in a skull, if there is a lateral force pushing on the neck region, the lateral force can deform the pressure sensing diaphragm 820 and cause an offset in reading. For example and without limitation, such side forces can result from tissue growth and/or shifts in tissue. The strain reliefs can isolate the side-loading force from diaphragm 820, and disperse the force elsewhere.

Standoff 851 can be at the end of implant body 808 proximal to the skull. The standoffs can facilitate the conduction of top-loading force along the walls of implant body 808. The top-loading force can be a result of the scalp pushing down the implant into the bone. If the side of implant body 808 proximal to the skull makes contact with the rounded skull near the center neck region, that contact point can act as a pivot and there can be a lever effect that causes additional deformation of diaphragm 820. The ridges of standoff 851 can bite into the skull bone or periosteum when the scalp holds the implant down. This can prevent the implant from sliding around and laterally within a burr hole. It can also allow external side loading forces to get loaded on the ridges instead of pushing on neck 850. Also, in some embodiments, neck 850 may be threaded such that ridges of neck 850 thread into a burr hole.

Figure 11:
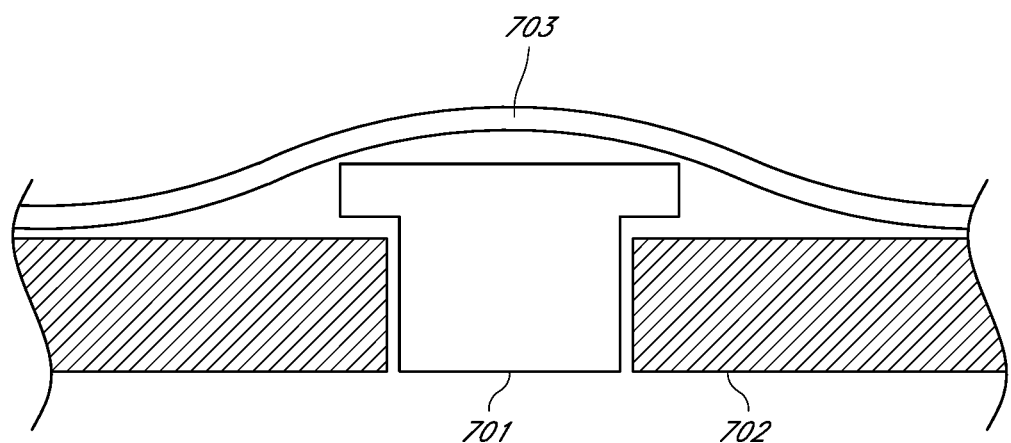
FIG. 11 illustrates an example implant retained in bone tissue by enclosing the device by surrounding skin tissue.

A number of structural supporting elements can be used to retain any of the implants described in this disclosure. In some embodiments, the implant can be retained in the biological tissue by securing additional biological tissue (e.g., bone tissue) around or onto said device in a fashion that restricts movement or migration of the device within, out of, or into the biological tissue. FIG. 11 illustrates an example implant retained in biological tissue by enclosing the implant by surrounding skin tissue. Implant 701 can be retained in biological tissue 702 by enclosing implant 701 by surrounding skin tissue 703. In some embodiments, the geometry of implant 701 can enable retention at the implantation site through unidirectional force as exerted by skin tissue 703. In other embodiments, the geometry of implant 701 can enable retention at the implantation site through multidirectional force exerted by a single or plurality of nearby tissue bodies.

Figure 12:
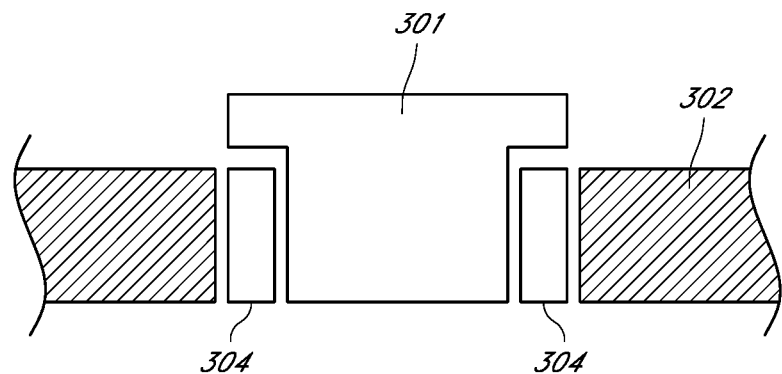
FIG. 12 illustrates an example implant retained by an example retaining gasket.

In some embodiments, an implant can be retained in the biological tissue by compressive or expansionary force that is coplanar to the implantation hole in the biological tissue. For example and without limitation, the implant can be retained using a radially outward directed structure and/or force. FIG. 12 illustrates an example implant retained by an example retaining gasket. A coplanar compressive force can be generated by retaining gaskets 304 when implant 301 is positioned in biological tissue 302. This force can hold implant 301 in place. In some embodiments, retaining gaskets 304 can be integral features of implant 304. In some embodiments, retaining gaskets 304 can be separate components that can be assembled with implant 301 prior to implantation into biological tissue 302. In some embodiments, retaining gaskets 304 can be formed from elastic or compressive materials such as, but not limited to, metal, rubber, silicone, plastic and the like. In some embodiments, retaining gaskets 304 can be shaped to have continuous contact with retained implant 301. In some embodiments, retaining gaskets 304 can be shaped not to have continuous contact with the retained implant 301. In some embodiments, retaining gaskets 304 can be shaped to have continuous contact with the perimeter of the hole in biological tissue 302 in which implant 301 is implanted.

Figure 13:
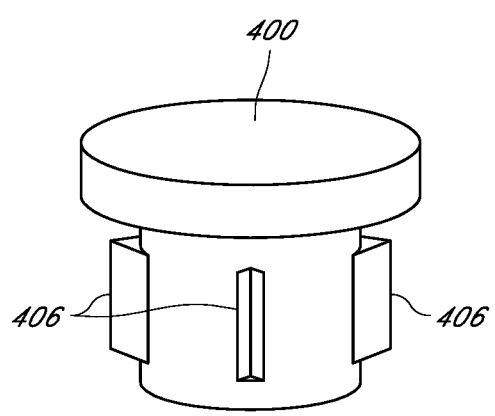
FIG. 13 illustrates an example implant having retaining protrusions.

FIG. 13 illustrates an example implant having retaining protrusions. For example and without limitation, protrusions can include a plurality of axially elongated ridges. In some embodiments, axially elongated ridges may be helical (e.g., the ridges of a screw) to retain the implant. For example and without limitation, retaining protrusions 406 of implant 400 can provide points of contact with the perimeter of the hole in the biological tissue in which implant 400 is implanted. In some embodiments, retaining protrusions 406 are fashioned as a single or array of spring-loaded levers or other such means of generating static compressive or expansionary force, such as, but not limited to metals, rubber, silicone, plastic and the like.

In some embodiments, an implant (e.g., any implant described in this disclosure) can be first inserted into a retaining mechanism to form an assembly, and then said assembly can be inserted into the biological tissue in which the implant is to be implanted. The implant can comprise one or more retaining mechanisms, such as sleeves, collars, and/or any other mechanisms described in this disclosure. In some embodiments, the retaining mechanism can include one or more tissue (e.g., bone and/or other biological tissues) engaging structures on the surface of a retaining structure. These tissue engaging structures can be radially directed outward from the retaining structure to the bone in order to engage the bone. The retaining structure may also have radially inward directed engagement structures in the inner surface in order to engage the implant. In some embodiments, the retaining mechanism can be first inserted into the biological tissue in which the implant is to be implanted, and then the implant can be inserted into the retaining mechanism that already resides in the biological tissue. In some embodiments, the insertion of the implant into the retaining mechanism that already resides in the biological tissue actuates, causes, or affects the compressive, expansionary, or deforming force that holds the implant in place within the implanted tissue. In some embodiments, the implant can be pushed axially into the retaining mechanism, wherein the radially inward directed structures of the retaining mechanism can engage the implant to form an assembly comprising the implant and retaining mechanism. Said assembly can then be implanted into the biological tissue.

Figure 14:
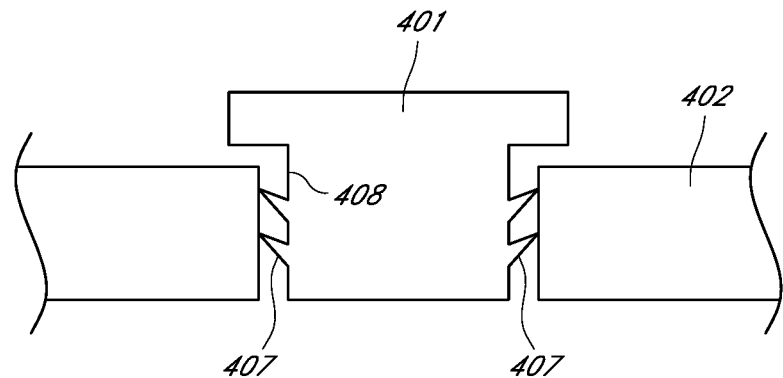
FIG. 14 illustrates an example implant having barbs.

In some embodiments, the implant can be retained permanently in the biological tissue by a retaining component such as, but not limited to, a screw or array of screws, non-elastic deformations, phase-changes, adhesion, unidirectional gates, locking mechanisms and the like that allows insertion of the device into the biological tissue in which it is implanted but resists removal. FIG. 14 illustrates an example implant having barbs to contact the surface of the biological tissue in which the implant is implanted. Implant 401 can incorporate barbs 407 (e.g., extending from surface 408) to contact biological tissue 402 in which implant 401 is implanted.

In some embodiments, the implant can be removable from the biological tissue after the desired period of fixed implantation by incorporation of features that enable or facilitate explantation such as, but not limited to, pull tabs, loops, ejection mechanisms and the like. In some embodiments, the features that enable and/or facilitate explantation are integral to the implant. In some embodiments, the features that enable or facilitate explantation are separate components, a multitude of separate components, or a combination of integral and separate components that are assembled with the implant prior to implantation.

Figure 15:
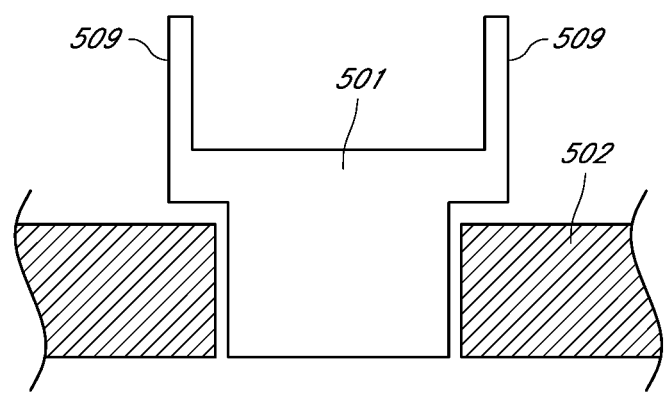
FIG. 15 illustrates an example implant retained by tabs that can be pulled to explant an implant.

FIG. 15 illustrates an example implant retained by tabs that can be pulled and/or twisted to explant an implant. Implant 501 includes tabs 509 that can be pulled to explant implant 501 from biological tissue 502 in which it is implanted. In some embodiments, the features that enable and/or facilitate explantation can be folded, stowed, tucked and/or otherwise stored to create a more suitable form factor for implantation and deployed for use at the time of explantation. In some embodiments, the tabs can work in conjunction with other retaining mechanisms described in this disclosure. For example, and without limitation, implant 501 can be retained in biological tissue 502 by a compressive force. Tabs 509 can be pulled in an axial direction. Tabs 509 can also be twist in a tangential direction so that implant 501 rotates while tabs 509 are pulled to facilitate explantation of implant 501. As another non-limiting example, the exterior surface of implant 501 may comprise threads so that the rotation of implant 501 can unscrew it (or screw it) from biological tissue 502.

Figure 16:
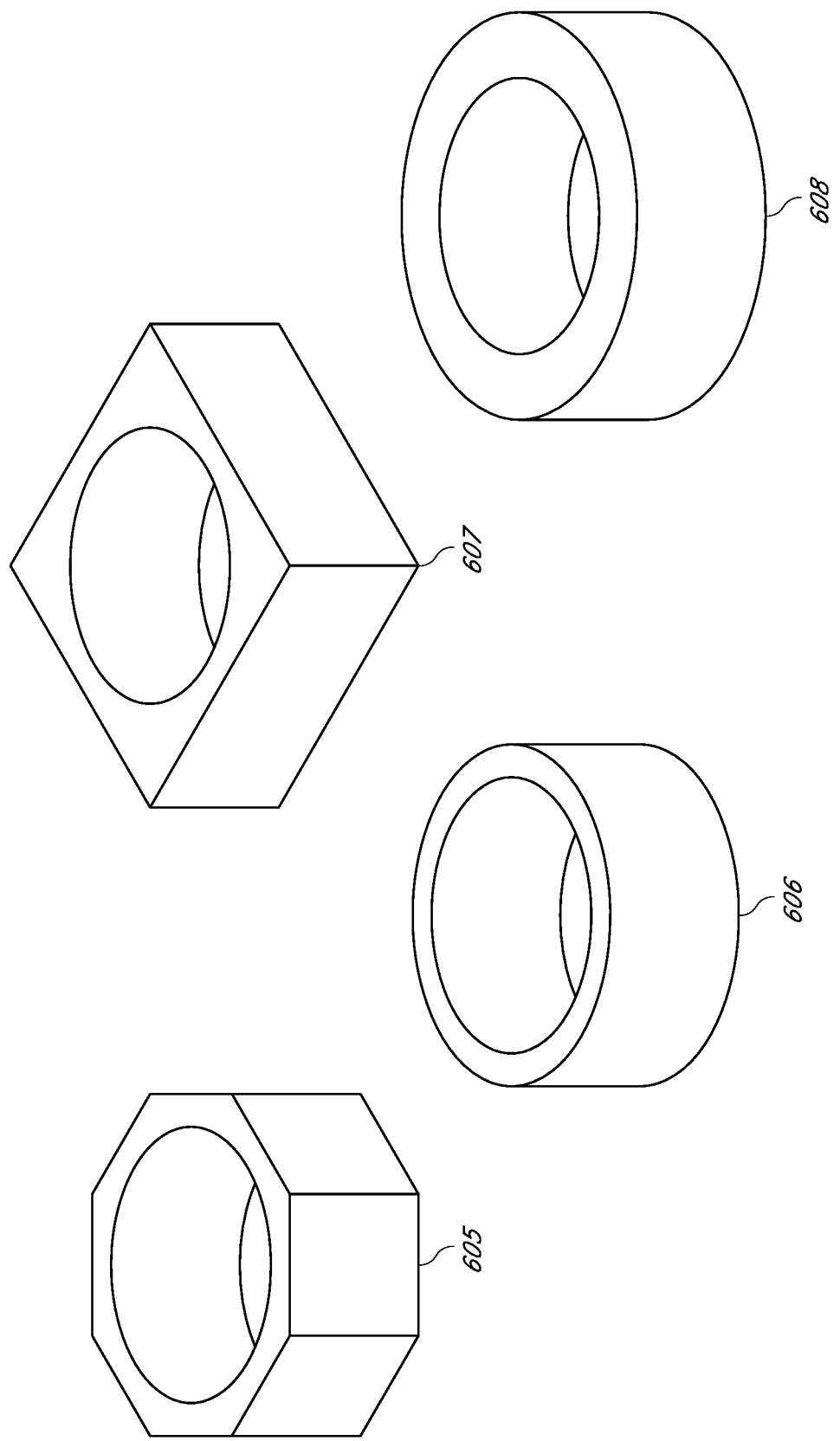
FIG. 16 illustrates example retaining gaskets.

FIG. 16 illustrates example retaining gaskets. In some embodiments, retaining gaskets can have an inner geometry suited for insertion of the implant and an outer geometry suited for insertion into the biological tissue in which the retaining gaskets are implanted. In some embodiments, the inner geometry can be configured for insertion of an implant and/or another retaining gasket (e.g., another retaining gasket in which an implant can be inserted). In some embodiments, retaining gaskets can have an outer geometry suited for insertion into other retaining gaskets. In some embodiments, retaining gaskets can have an outer geometry suited for insertion into the biological tissue in which the retaining gaskets are implanted. A plurality of retaining gaskets can enable a user to retain an implant, as in any implant described in this disclosure, in a variety of geometries of holes in biological tissues by selecting a single retaining gasket or by configuring multiple retaining gaskets to suit the geometry of the holes. Retaining gaskets can vary in geometries, including shapes such as octagons, circles, and squares as desired. Similarly, the retaining gaskets can also vary in dimensions, including thickness, length, height, size, and/or any other geometric dimension as desired.

For example, and without limitation, retaining gasket 605 can have an upper edge and a lower edge, and sidewalls therebetween. Retaining gasket 605 can have a central lumen traversing the upper edge and lower edge. The outer surface of the side walls may comprise tissue engaging structures for engaging the surface of tissues (e.g., bone and/or other biological tissue) proximal to the side walls. The tissue engaging structures may be any of the tissue engaging structures described in this disclosure. The interior surface of the central lumen may be configured to engage an implant (e.g., any implant described in this disclosure). In some embodiments, the inner surface may be threaded and/or have structures directed radially inward to engage the implant. The inner surface may also comprise any implant-engaging structure described in this disclosure. For example, and without limitation, a retaining gasket can be an octagon as illustrated in retaining gasket 605, circular as illustrated in retaining gasket 606, a square as illustrated in retaining gasket 607, and/or any other geometry as desired. The dimensions of the retaining gasket can also vary as illustrated by retaining gasket 608, which is a circular retaining gasket that is longer, wider, and thicker than circular retaining gasket 606.

Figure 17:
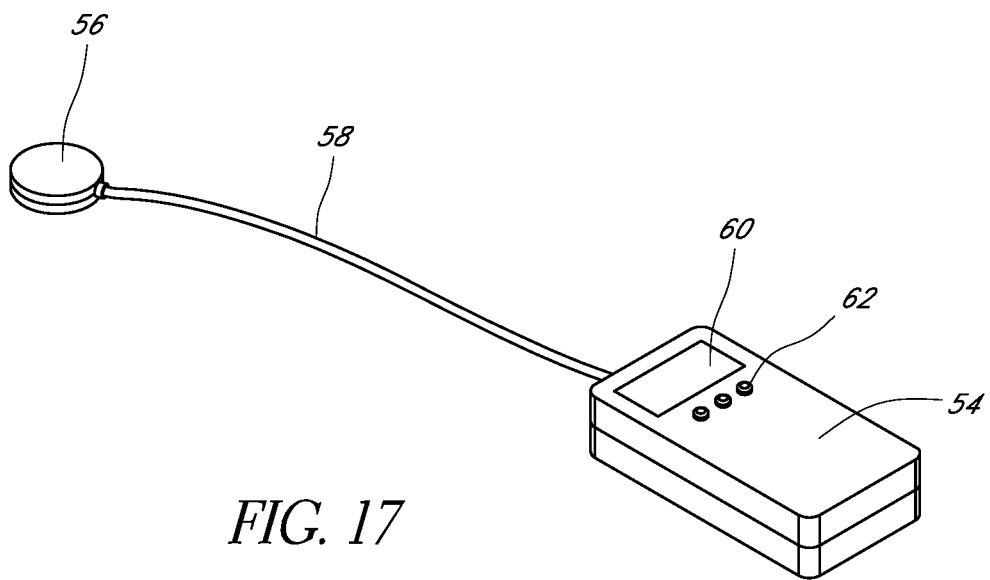
FIG. 17 illustrates a perspective view of an example transceiver.

FIG. 17 illustrates a perspective view of an example transceiver. In some embodiments, transceiver 4 includes antenna 56, which can be connected by cable 58 to transceiver body 54. In some embodiments, antenna 56 can be fixed to cable 58 permanently. In some embodiments, antenna 56 can be plugged into and unplugged from cable 58. In some embodiments, cable 58 can be fixed to transceiver body 54 permanently. In some embodiments, cable 58 can be plugged into and unplugged from the transceiver body 54.

In some embodiments, transceiver 4 can be communicatively coupled with an implant (e.g., implant 2 and/or any implant described in this disclosure) to transmit power and/or data. Having a protocol for communicative coupling transceiver 4 and an implant may be advantageous in order to pair transceiver 4 with a particular implant. Such may be desirable for safety, such as in order to prevent errant modifications to implants (e.g., modifications to other implants such as pacemakers and/or other implants in the patient and/or implants in other patients). Also, such a protocol may be desirable for security, such as preventing unauthorized access to implant programming and/or powering. In some embodiments, transceiver 4 can also maintain an updatable list of implant identification ("ID") parameters in memory including, without limitation, identification numbers, model numbers, power usage characteristics, power frequencies, data frequencies, data usage characteristics and protocols, processor numbers, and/or other unique identifiers and/or combination of unique identifiers. An implant can send its identifier to the implant (e.g., via any of the means that are described below) and transceiver 4 can check if the implant is in its updatable list of implant ID parameters. If the implant is on the updatable list, transceiver 4 and the implant can communicatively couple. Other ways of pairing an implant and transceiver 4 can also be used in combination or in the alternative. For example and without limitation, password and key systems known in the art can be used to authenticate a pairing between an implant and transceiver 4 (e.g., a public/private key pairing system).

In some embodiments, the protocol for communicative coupling can use the data and/or power signals used by the implant and/or transceiver 4 to transmit/receive data and/or power. For example, and without limitation, transceiver 4 can be paired with an implant using data information sent over data communication protocols. For example and without limitation, information can be sent via the data antenna (e.g., data antenna 837) by using password and key systems known in the art (e.g., public/private key pairing). In some embodiments, an implant can send a signal with a particular frequency and/or modulation from the implant's power antenna in order to operably couple data and/or power transmission to transceiver 4. In some embodiments, transceiver 4 can send a power signal to an implant. The implant can then adjust its power consumption, which can be detected by transceiver 4 via a reverse link, where, for example, transceiver 4 detects changes in the load placed on its power circuitry due to the implant's power consumption. Based on the pattern of the changes in load (e.g., changes in the load's frequency, amplitude, etc.), transceiver 4 can determine (e.g., by checking if the pattern corresponds to an implant on its updatable list of implants) whether to communicatively couple with the implant for data and power transmission/reception.

In some embodiments, communicative pairing can be achieved using an out-of-band system (e.g., an out-of-band authentication system), where identification is transmitted/received using a different frequency, protocol, channel, and/or hardware than data and/or power. For example, and without limitation, transceiver 4 can pair with an implant using near field communication ("NFC"), such as, without limitation, radio frequency identification ("RFID"). Using NFC may be advantageous because NFC can have a confined range, which can limit communication between implant and transceivers to those that are in close proximity to each other. For example and without limitation, in some embodiments, NFC can initiate a connection only where the implant and transceiver are less than 10 cm apart. A person having ordinary skill in the art should appreciate that the range can be adjusted based on known design choices. In some embodiments, a user interface can be used at transceiver 4 in order to select an implant to communicatively pair for transmitting and/or receiving data and/or power.

Figure 18:
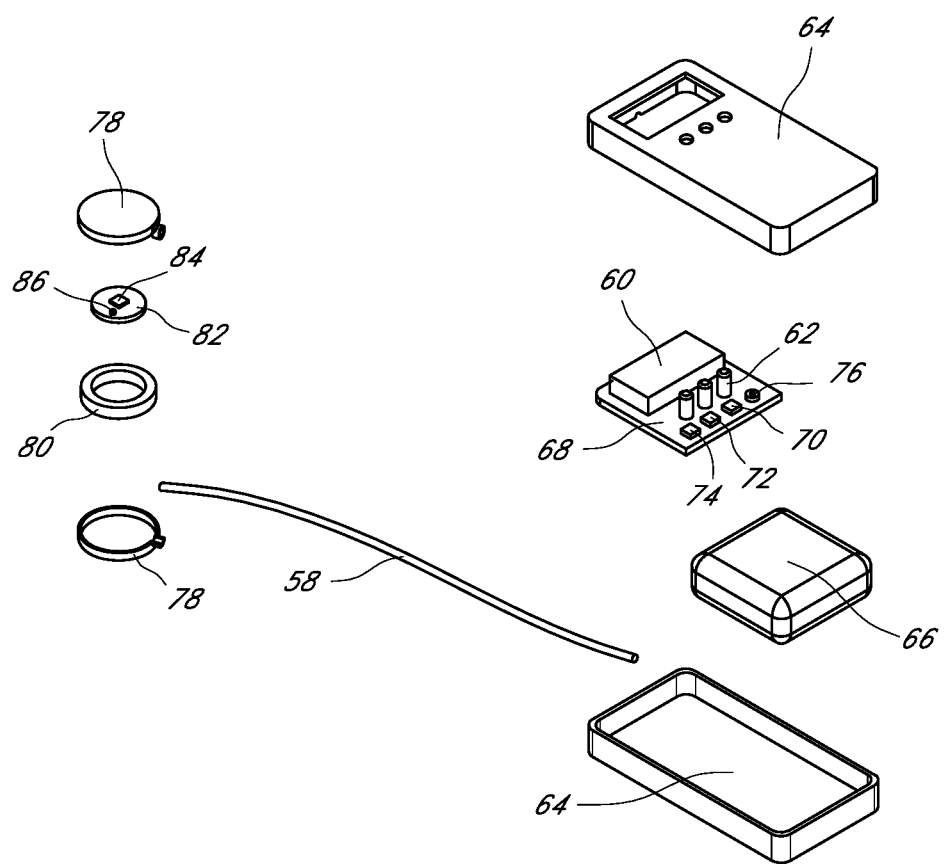
FIG. 18 illustrates a perspective exploded view of the example transceiver illustrated in FIG. 17.

FIG. 18 illustrates a perspective exploded view of the example transceiver illustrated in FIG. 17. In some embodiments, antenna 56 can include enclosure 78, which can house power-transmitting coil 80, which sends power to an implant (e.g., implant 2 of FIG. 3), including an electronics assembly of the implant. In some embodiments, power transmitting antennae geometries other than a coil can be implemented to transmit power. In some embodiments, electronics assembly 82 includes a temperature sensing system that can be used to diagnose operational temperature of the transmitting antenna and alert the system of temperatures that can injure the subject, damage the system, or impact performance. In some embodiments, electronics assembly 82 can include a barometric pressure sensing system that can be used to measure barometric conditions to compensate pressure measured by an implant (e.g., implant 2 of FIG. 3) for barometric affects. In some embodiments, electronics assembly 82 can include a position sensor to establish antenna motion, position, orientation, and the like. Antenna position can be used to infer implant position as well as patient position, which are data that can be used to interpret physiological measurements affected by position. Certain physiological parameters, such as intracranial pressure, are significantly impacted by subject position. For example, a subject in an upright position has a lower ICP than the same subject in the same physiological state in a supine position. As such, when interpreting pressure measurements for intracranial pressure, it can be desirable to consider changes in ICP due to subject position, which can enable determinations of whether changes in measured ICP are due to factors other than position, such as due to ailment, injury, condition, and so forth. In some embodiments, data antenna 86 can be included in the electronics assembly 82. In some cases, placing data antenna 86 inside transceiver antenna 56 can significantly shortens the telemetry range to an implant in contrast to placing data antenna 86 within transceiver body 54. Decreasing the range of telemetry can increase the quality of service. It can also lower power demand for data transmission.

In some embodiments, transceiver body 54 can incorporate display screen 60 for display output to the user, user input buttons 62, electronics assembly 68, and power source 66 housed within enclosure 64. Enclosure 64 can protect transceiver body 54 from operational hazards, such as (and without limitation) drops, splashes of liquid, and impacts. Enclosure 64 can also enable attachment of transceiver body 54 to the subject, a patient bed, or other fixtures as desired. In some embodiments, display screen 60 can output measured parameters, system operational state, system identification, subject identification, other information, or a combination thereof. Examples of display screens 60 include, but are not limited to, liquid crystal displays, e-ink displays, segmented displays, and the like. In some embodiments, as depicted in FIG. 18, user input buttons 62 can be implemented to allow user operation of the system. In other embodiments, user input buttons can be substituted with touch screens, scroll wheels, track pads, keyboards, and other alternatives. In some embodiments, the electronics assembly 68 includes one, or multiple, printed circuit boards that incorporate processor modules 74, analog-to-digital converter modules 72, telemetry modules 70, and various sensors 76. In some embodiments, processor modules 74 are capable of data storage. In some embodiments, sensors 76 are barometric sensors, temperature sensors, position sensors, motion sensors, and the like. Transceiver electronics assembly 68 can be powered by a power source 66. In some embodiments, power source 66 can be a disposable or rechargeable battery. In some embodiments, power source 66 can be mains electricity. Alternative power sources 66 can include, without limitation, solar cells, fuel cells, and the like.

Figure 19:
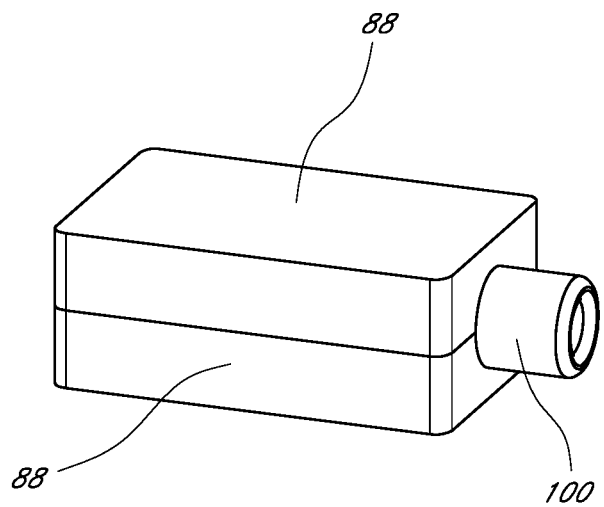
FIG. 19 illustrates a perspective view of an example receiver interface.
Figure 20:
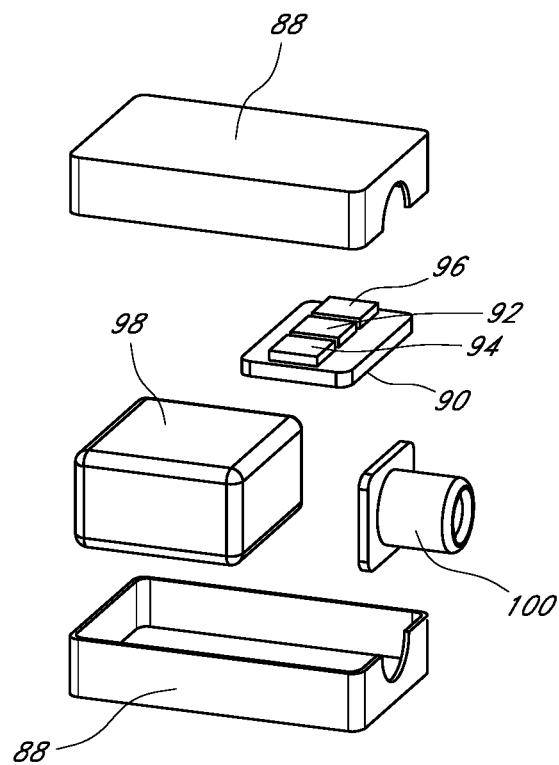
FIG. 20 illustrates a perspective exploded view of the example receiver interface illustrated in FIG. 19.

FIG. 19 illustrates a perspective view of an example receiver interface. FIG. 20 illustrates a perspective exploded view of the example receiver interface illustrated in FIG. 19. In some embodiments, receiver interface 6 (FIG. 2) can comprise a portable enclosure 88 with port 100 for connection to an external system. Receiver interface 6 can incorporate electronics assembly 90, a power source 98, and an interface port 100. In some embodiments, electronics assembly 90 can include one, or multiple, printed circuit boards that incorporate processor modules 92, digital-to-analog converter modules 94, and telemetry modules 96. In some embodiments, receiver interface 6 can also incorporates sensors. In some embodiments, receiver interface 6 can incorporate user input and display means. In some embodiments, receiver interface 6 can connect with external systems by plugging directly in a port on the external system. In some embodiments, receiver interface 6 can connect to external systems through a cable. In some embodiments, receiver interface 6 can connect to external system through wireless communication means. In some embodiments, electronics assembly 98 of receiver interface 6 can be powered by power source 98. In some embodiments, power source 98 can be a disposable or rechargeable battery. In some embodiments, power source 98 can be mains electricity. In some embodiments, power source 98 may not be incorporated into receiver interface 6, which can draw power from the external system. Alternative power sources 98 can include, for example and without limitation, solar cells, fuel cells, and the like.

In some embodiments, physiological measurements can be compensated for environmental, situational, positional, or other physiological factors that impact the measurement. The disclosed system can enable inclusion of sensing, measurement, or input of these factors at each of the system components, which can include implant 2, transceiver 4, and receiver interface 6 (FIG. 2). Processing for compensation can be implemented by implant 2, transceiver 4, receiver interface 6, and/or a combination thereof. Processing can be implemented with analog circuitry, digital circuitry, or a combination of both.

Figure 21A:
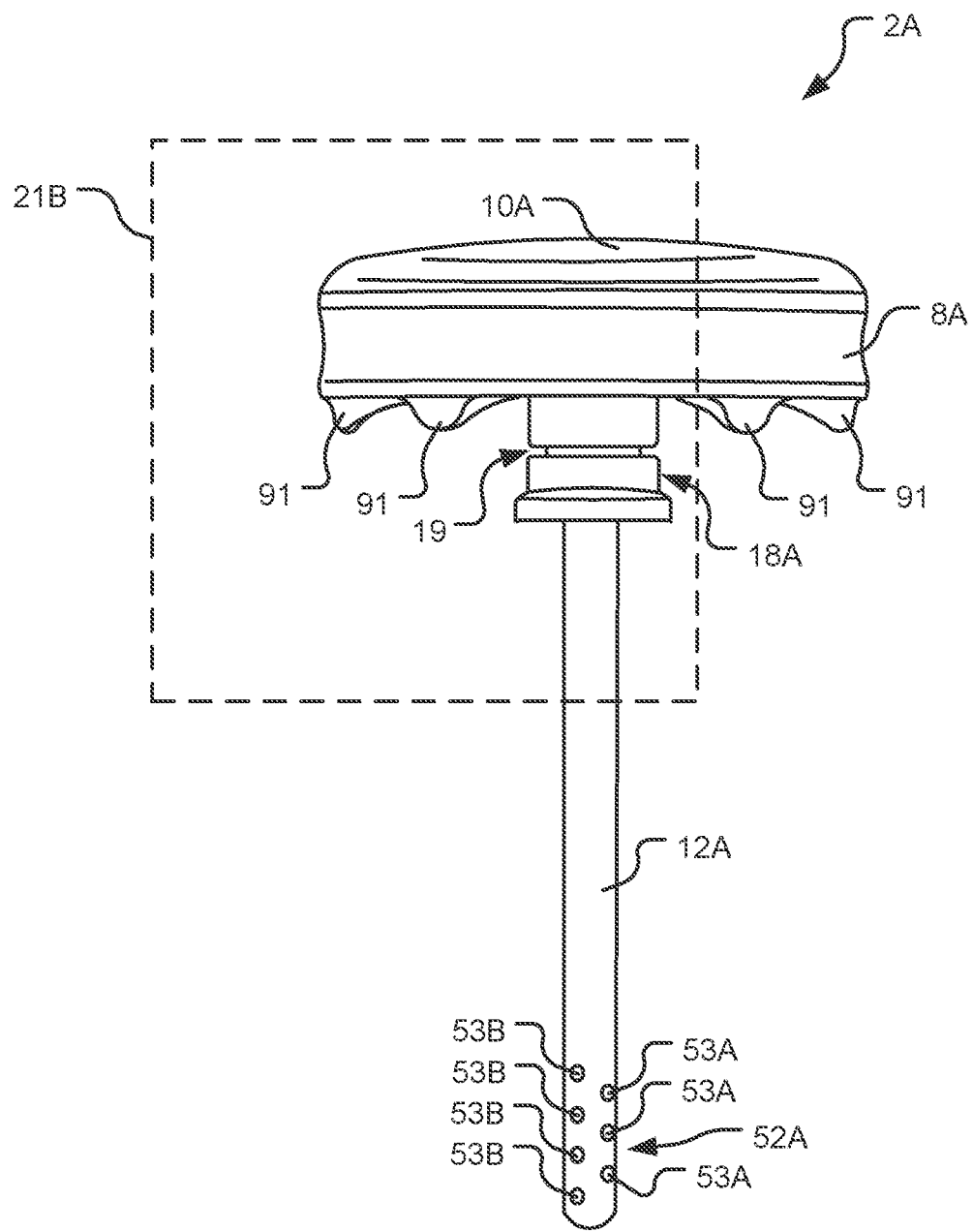
FIGS. 21A-21C illustrate various views of another example implant.
Figure 21B:
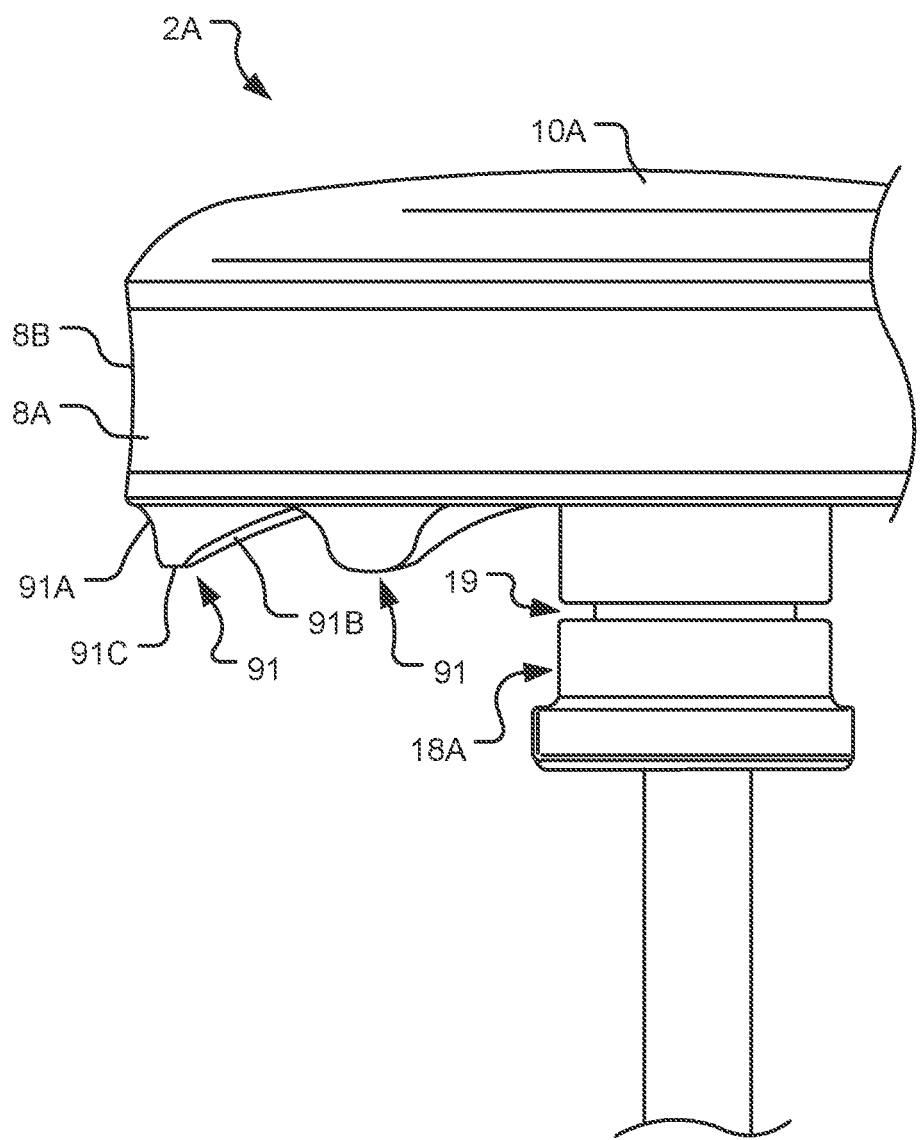
Figure 21C:
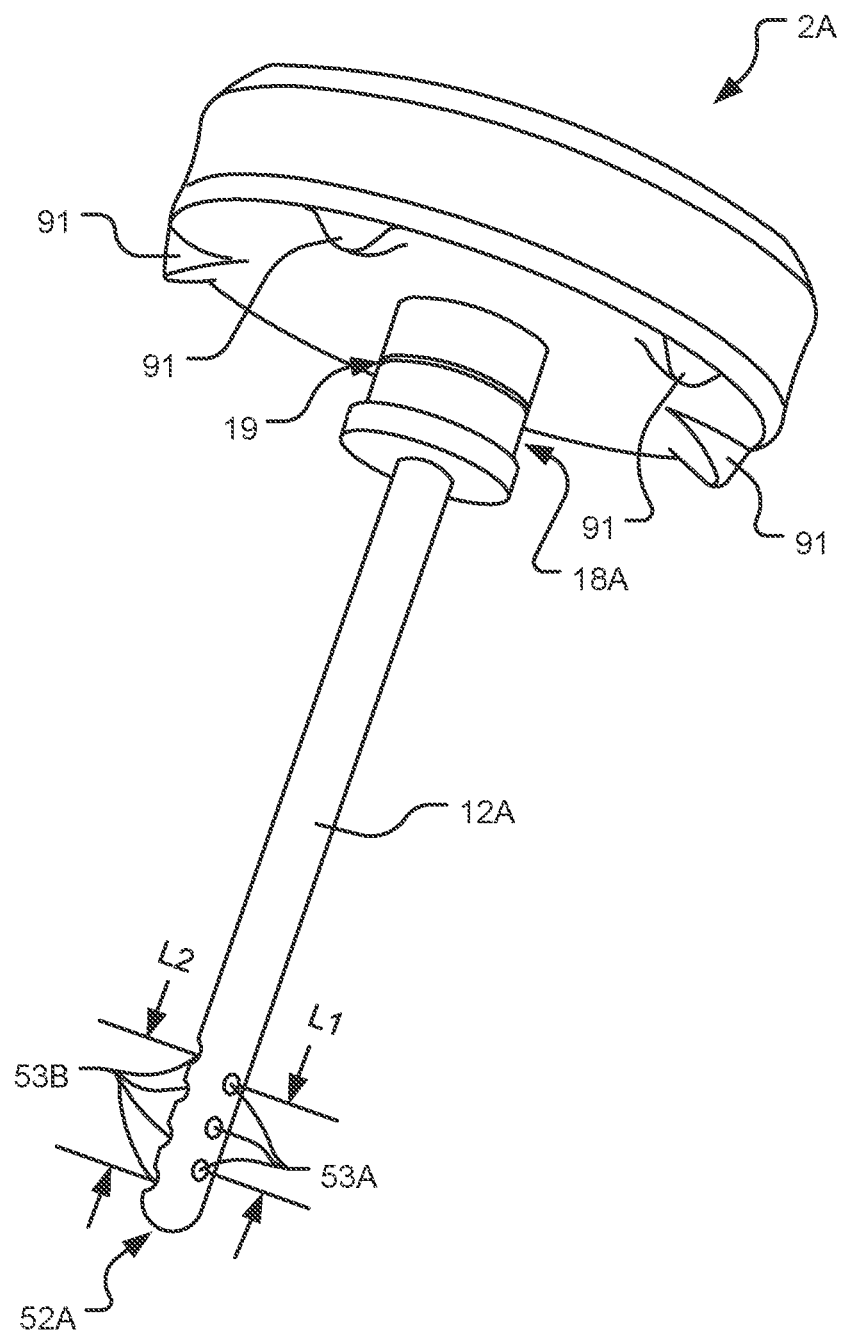

FIGS. 21A-21C illustrate various views of another example implant 2A. FIG. 21A is a side view of the implant 2A, FIG. 21B is a detail view of the implant 2A taken from FIG. 21A as indicated by detail 21B, and FIG. 21C is a perspective view of the implant 2A. The implant 2A may have the same or similar features as other implants described herein, for example the implant 2, and vice versa. In some embodiments, the implant 2 in addition or alternatively has the features described below. In some embodiments, the implant 2A in addition or alternatively has the features described herein with respect to other implants, for example the implant 2.

Referring to FIGS. 21A-21C, the implant 2A may have an implant body 8A coupled with a pressure conduction catheter 12A, which may have the same or similar features as other implant bodies and pressure conduction catheters described herein, respectively, for example the implant body 8 and the pressure conduction catheter 12. The implant 2A may further have a neck 18A, which may have the same or similar features as other necks described herein, for example the neck 18 as shown in FIG. 6. The implant body 8A may further include an implant cap 10A, which may have the same or similar features as other implant caps described herein, for example the implant cap 10.

The implant 2A may further include one or more standoffs 91. The standoffs 91 may be protrusions that extend from the implant body 8A. As shown, the standoffs 91 protrude in the distal direction from a distal side of the implant body 8A. The standoffs 91 may be approximately ramp-shaped with a triangular cross-section. The standoffs 91 may extend further distally near a radially outer portion of the standoffs 91 as compared to an inner portion. Thus, the standoffs 91 may be angled such that a portion or portions of the standoffs 91 that is radially farther outward from a central axis of the implant 2A are extending distally farther than a portion or portions of the standoffs 91 that is radially farther inward.

The standoffs 91 may be integral with a portion or portions of the implant 2A. In some embodiments, the standoffs are integral with the implant body 8A. The standoffs 91 and implant body 8A may thus be monolithic. The standoffs 91 and implant body 8A may be formed from the same piece of material.

In some embodiments, the standoffs 91 may be separate parts that are attached to or otherwise connected with the implant 2A, such as to or with the implant body 8A. In some embodiments, there may be one or more intermediate structures in between the standoffs 91 and the implant 2A. For example, there may be attachment brackets or fittings on the implant body 8A to which the standoffs 91 may be attached or otherwise connected. The standoffs 91 may be fastened, adhered, strapped, welded, or otherwise coupled with the implant body 8A, or combinations thereof.

The standoffs 91 may be formed from a variety of suitable materials. In some embodiments, the standoffs 91 are formed from metal, such as titanium. The standoffs 91 may be formed from other metals and/or metal alloys, and/or other materials, such as plastic, polymers, rubbers, other suitable materials, or combinations thereof. The standoffs 91 may be formed from these and other materials regardless of whether the standoffs 91 are integral parts with or are separate parts with the implant body 8A (or with other portions of the implant 2A). The standoffs 91 may thus be rigid materials, soft materials, semi-rigid or semi-soft materials, etc., or combinations thereof.

The standoffs 91 may each include one or more contact surfaces 91C (see FIG. 21B). The contact surface 91C may be located near or at the outer radius or edge of the implant 2A, such as at or near the outer radius or edge of the implant body 8A. The contact surfaces 91C may be relatively small, flat surfaces. In some embodiments, the contact surfaces 91C may be larger, rounded, curved, etc. For instance, the contact surfaces 91C may have a topography that complements that of a corresponding skull structure adjacent to a cranial burr hole. The contact surfaces 91C may thus contact the skull when the implant 2A is implanted. For example, the implant 2A may contact the skull along the various contacts surfaces 91C of the standoffs 91. This may prevent or reduce contact of the implant 2A along, near, or at a portion or portions of the implant body 8A near the neck 18A. Thus, forces acting in a distal direction on the implant 2A will have a line of action primarily or entirely through the standoffs 91, thus decreasing or removing those forces from acting through the neck 18A or through portions of the implant body 8A in the neck 18A region. Removing or reducing forces acting through this neck 18A region may decrease or remove stresses and strains imposed on the implant body 8A near a diaphragm of the implant 2A, which may have the same or similar features as other diaphragms described herein, for example the diaphragm 20 of the implant 2 shown in FIG. 5B. Thus, removing or reducing forces acting through this neck 18A region may reduce or remove any deformation of the diaphragm that may be due to axial loading on the implant and the corresponding reaction forces from the skull or other structures creating such reaction forces.

In some embodiments, the standoffs 91 may include outer surfaces 91A and inner surfaces 91B (see FIG. 21B). The outer surface 91A may extend from an outer edge 8B of the implant body 8A to the contact surface 91C. The outer surface 91A may be steep and slightly curved inward as shown. The outer surface 91A may have other suitable shapes and configurations. The inner surface 91B may have a relatively shallower angle as compared with the outer surface 91A and may be approximately flat. The inner surface 91B may have other suitable shapes and configurations. In some embodiments, a continuous surface may be formed from the outer surface 91A to the contact surface 91C to the inner surface 91B. The inner surface 91B may extend to a flat or approximately flat region of the underside of the implant body 8A.

There may be multiple standoffs 91. As shown, there may be five standoffs 91 angularly and evenly spaced about a central axis of the implant 2A and along an outer region of the implant body 8A. This is merely one example. In some embodiments, there may be two, three, four, six, seven, eight, nine, ten, eleven, twelve, thirteen, fourteen, fifteen, sixteen, seventeen, eighteen, nineteen, twenty, or more standoffs 91. The standoffs 91 may be positioned angularly along the outer edge of the implant 2A in a variety of configurations, positions, spacings, etc. In some embodiments, the standoffs 91 may be unevenly spaced angularly about a central axis of the implant 2A. As shown, the standoffs 91 may all be positioned radially the same distance from the central axis. In some embodiments, the standoffs 91 may not all be positioned radially the same distance from the central axis. For example, some of the standoffs 91 may be located near or along the outer edge 8B of the implant body 8A while others may be positioned farther inward radially. Further, the standoffs 91 may or may not all extend the same distance distally from the implant 2A. For example, standoffs 91 located near the outer edge 8B may extend farther distally then standoffs 91 located radially farther inward from the outer edge 8B.

As further shown, the implant 2A may include a contoured outer edge 8B (see for example FIG. 21B). The outer edge 8B may be an outer wall of the implant body 8A. The outer edge 8B may be curved slightly radially inward. This is merely one example and other suitable configurations of the outer edge 8B may be implemented.

The implant 2A may further include various stress relief features. These features may prevent or reduce deformation or other mechanical effects due to loading on the implant 2A. As shown, the neck 18A may include a recess 19. The recess 19 may be a portion of the neck 18A with a smaller outer width. For instance, the recess 19 may be a portion of the neck 18A with a smaller radius than an adjacent portion or portions of the neck 18A. The recess 19 may thus be formed or otherwise defined by the neck 18A. The recess 19 may extend circumferentially around the neck 18A. As shown, the recess 19 may extend entirely around the neck 18A, for example a full three hundred and sixty degrees. In some embodiments, the recess 19 may extend less than three hundred and sixty degrees. In some embodiments, there may be multiple such recesses 19. For instance, there may be two, three, four or more recesses 19. Further, there may be multiple full or partial recesses located at different locations longitudinally along the axial direction of the neck 18A. For example, there may be two of the recesses 19 as shown, one above the other. This is merely one example and other suitable configurations may be employed.

The recess 19 may facilitate absorbing side loading forces on the neck 18A. Such forces may be due to for example incorrect or misaligned insertion of the implant 2A, a misaligned or off-angle burr hole, etc. Such forces may induce loading and/or deformation on the implant 2A which may for example deform the diaphragm. The recess 19 may assist with preventing such forces from affecting the diaphragm and/or other parts of the implant 2A. For instance, the recess 19 may serve as a stress concentrator or stress riser that redirects or sinks surface stress away from the structure or structures supporting the diaphragm, sensors, electronics, etc.

The implant 2A may not include a barrier, such as the barrier 813. The implant 2A may thus have a catheter 12A with a bare distal end 52A. The catheter 12A may thus have ports 53A, 53B exposed to the intracranial environment when implanted. The ports 53A, 53B may thus be open to the implanted setting, allowing pressure to be conducted up to the diaphragm via intracranial fluid and/or air. With typical designs, the lack of a barrier such as a sheath may increase the risk of occlusion of the ports of a catheter. Thus, the ports 53A, 53B are designed to address and mitigate this risk, thus providing a simpler and less complex implant (i.e. no barrier needed) while still achieving the desired functionality of the catheter 12A. Various design approaches with the ports 53*a*, 53B may be employed with respect to, for example, port size, location, relative location to each other, absolute location for example with respect to the catheter tip or to target pressure sensing region of the brain, configuration, pattern, alignment, etc. In some embodiments, the ports 53A, 53B are relatively larger or smaller than typical catheter ports. For instance, the ports 53A, 53B may have larger diameters relative to the ports 853 described herein, for example with respect to FIG. 9. Further, the lack of a barrier may allow for a variable length, e.g. shorter, longer, adjustable length, etc., catheter 12A. For instance, the length of the catheter 12A without any barrier may be relatively shorter than the length of the catheter 812 having the barrier 813, as described herein. Thus, the implant 2A may be less invasive than other implants. In some embodiments, the length of the catheter 12A without any barrier may be relatively longer than the length of the catheter 812 having the barrier 813, as described herein. For instance, if a longer or larger port 53A, 53B pattern is desired or necessary, the catheter 12A may be longer. In some embodiments, the length of the catheter 12A may be adjusted for a custom fit. For example, the catheter 12A enables trimming or otherwise shortening of the length of the catheter 12A, which may be at the time of implantation, to customize where the distal sensing region, i.e. the region with the ports 53A, 53B, ends up in the patient. For instance, the surgeon can cut the distal end 52A to the desired length based on patient needs. In some embodiments, the catheter 12A may be supplied with a longer length and initially unattached attached to, but configured to couple with, the implant body 8A, for example with the neck 18A. Then, at the time of implantation, the surgeon or other user can trim the catheter (either with or without a barrier) to the desired length and attach it to the implant body 8A. Thus, the depth of monitoring (epidural, subdural, depth in parenchyma, ventricular, etc.) may be configured or otherwise customized for a particular patient, procedure, etc.

The catheter 12A may have multiple ports 53A and multiple ports 53B. In some embodiments, there may be a column or columns of the ports 53A and a column or columns of the ports 53B. For instance, there may be two columns of the ports 53A and two columns of the ports 53B. The columns of the ports 53A, 53B may be spaced generally evenly or unevenly about a central axis of the implant 2A. For instance, a first column of the ports 53A may be spaced angularly ninety degrees from a first column of the ports 53B, a second column of the ports 53A may be located one hundred eighty degrees angularly from the first column of the ports 53A, and a second column of the ports 53B may be located one hundred eighty degrees angularly from the first column of the ports 53B. This is merely an example and other suitable locations and/or spacings may be implemented. Further, the columns of the ports may have various lengths. As shown in FIG. 21C, the ports 53A may be arranged in a column of length L1, while the ports 53B may be arranged in a column of length L2. In some embodiments, the length L1 may be shorter than the length L2. In some embodiments, the length L1 may be longer than, or the same as, the length L2.

Figure 21D:
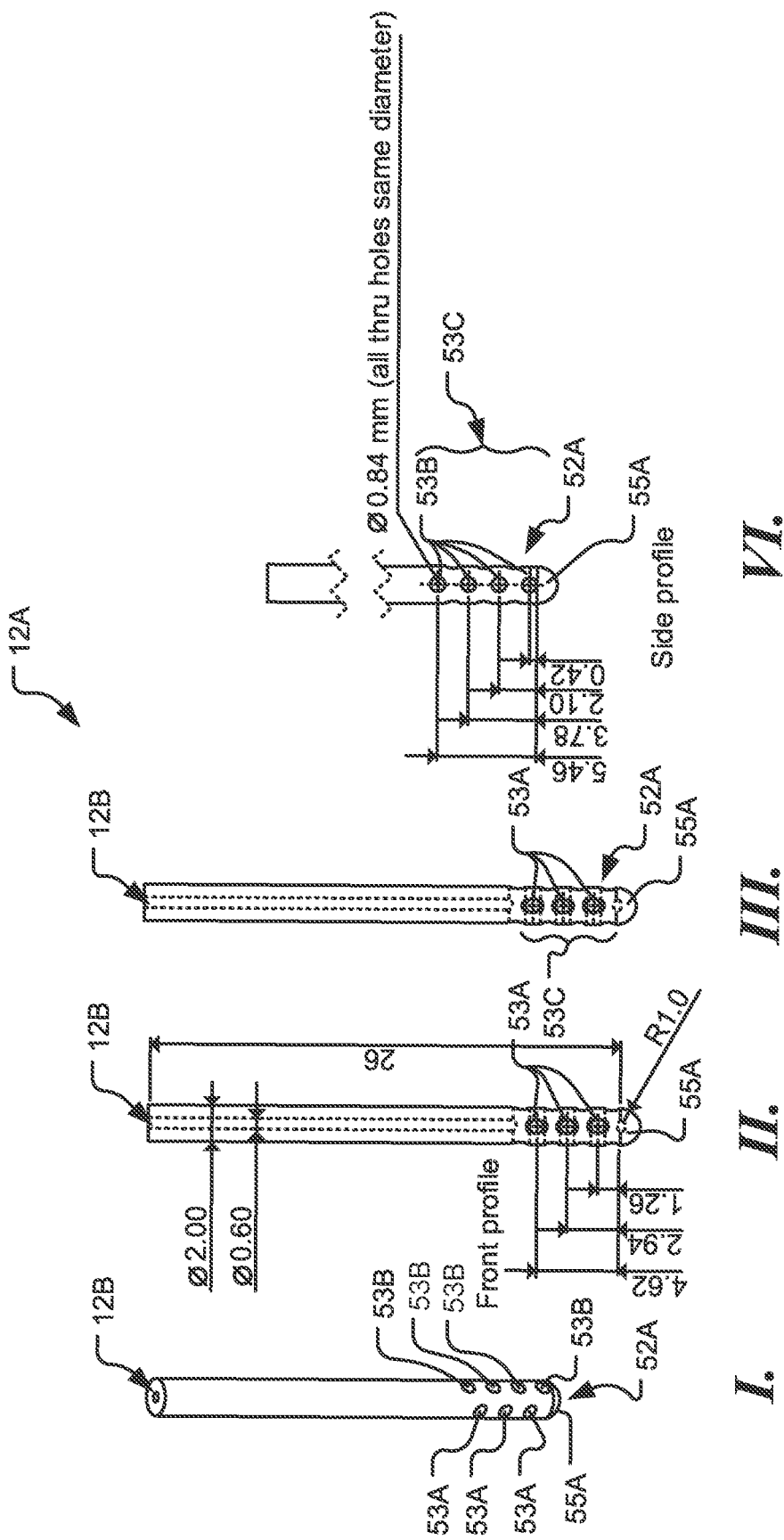
FIG. 21D illustrates various views of an example pressure conduction catheter that may be used with the various implants described herein.

FIG. 21D illustrates various views of an example pressure conduction catheter 12A that may be used with the various implants described herein, for example the implant 2A. As mentioned, the catheter 12A can have various configurations of the ports 53A, 53B, for example various diameters, layouts, etc. Parts I-IV of FIG. 21D show one such configuration. In FIG. 21D, part I shows a perspective view of the catheter 12A, parts II and III show front profile views of the catheter 12A, and part IV shows a side profile view of the catheter 12A.

As shown, the catheter 12A may have an inner lumen or hole 12B extending through the length of the catheter form the distal end 52A with the ports 53A, 53B to a proximal end that couples with the implant body, such as the implant body 8A. In some embodiments, the inner diameter of the catheter 12A, i.e. the outer diameter of the hole 12B, may be about 0.60 millimeters. In some embodiments, the outer diameter of the catheter 12A may be about 2 millimeters. These are merely examples and other dimensions may be implemented.

The distal end 52A of the catheter 12A may include an endpiece 55A. The endpiece 55A may be a cap or other similar structure that couples with the distal end 52A of the catheter 12A. The endpiece 55A may be the same or similar material as the catheter 12A, and may provide a closing to the distal end 52A of the catheter 12A, for example if the catheter 12A is trimmed or otherwise adjusted lengthwise for a custom fit. In some embodiments, the catheter 12A is trimmed to a desired length and then the endpiece 55A is attached to close the open end of the catheter 12A that may result after trimming.

The catheter 12A may include a pressure sensing zone 53C. As shown, the zone 53C may be located near the distal end of the catheter 12A. The zone 53C may include the one or more ports 53A, 5B. The zone 53C may also include portions of the catheter 12A that do not include any ports. The zone 53C may provide a region where pressure is to be sensed using the catheter 12A. The zone 53C may provide a region where the catheter 12A may be trimmed or otherwise adjusted lengthwise. For instance, the catheter 12A may be cut within the zone 53C to shorten the catheter 12A for a custom fit. The zone 53C may have a flat outer wall, or as shown it may include circumferential grooves along the outer surface of the catheter 12A in the zone 53C (see for example parts II-IV of FIG. 21D). Such grooves or other similar features in the zone 53C may improve performance of the catheter 12A, for example providing stability or improved pressure readings. These features may also provide means for trimming or otherwise adjusting the length of the catheter 12A, for example by providing weak points where the catheter 12A may be more easily cut.

As shown, the ports 53A may be arranged longitudinally along a front side (parts II and II of FIG. 21D). The ports 53A may be located various distances from a distal portion of the catheter 12A, e.g. from a portion that couples with the endpiece 55A. In some embodiments, a first port 53A is located 1.26 millimeters from the distal portion, a second port 53A is located 2.94 millimeters from the distal portion, and a third port 53A is located 4.62 millimeters from the distal portion. Further, the ports 53B may be arranged longitudinally along a side that is located angularly about ninety degrees relative to the front side (part IV of FIG. 21D). The ports 53B may be located various distances from a distal portion of the catheter 12A, e.g. from a portion that couples with the endpiece 55A. In some embodiments, a first port 53B is located 0.42 millimeters from the distal portion, a second port 53B is located 2.10 millimeters from the distal portion, a third port 53B is located 3.78 millimeters from the distal portion, and a fourth port 53B is located 5.46 millimeters from the distal portion. The various ports 53A, 53B may have a diameter of about 0.84 millimeters. In some embodiments, the ports 53A, 53B may have a diameter between about 0.5 and 1 millimeter. In some embodiments, the ports 53A, 53B may have a diameter that is smaller or larger than these sizes. Further, the ports 53A, 53B may not all be the same size.

Figure 22A:
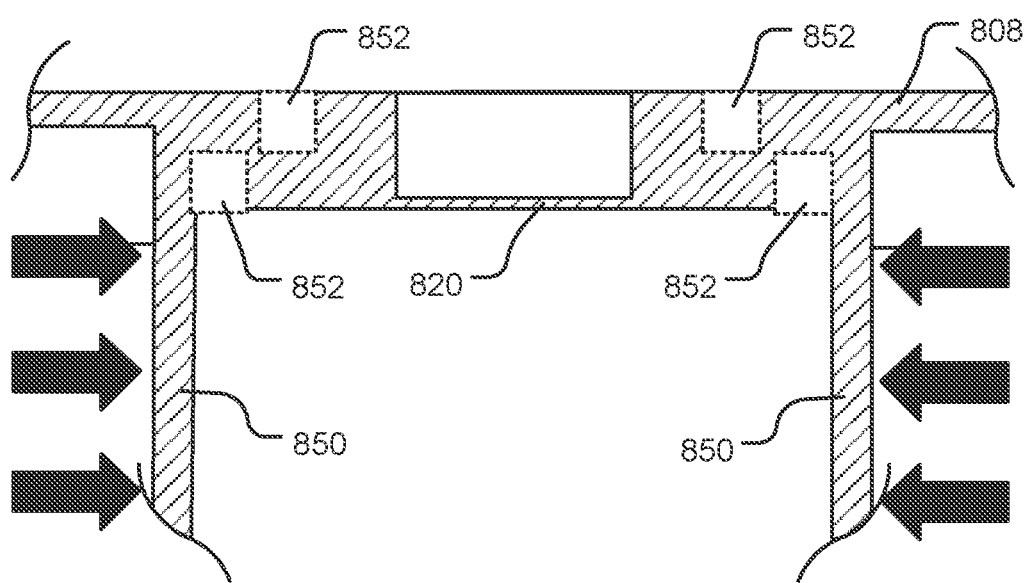
FIGS. 22A-22B illustrate partial cross-section views of example implant bodies that may be used with the various implants described herein.

FIG. 22A illustrates a partial cross-section view of the implant body 808 that may be used with the various implants described herein. The implant body 808 may include the neck 850 and diaphragm 820, as previously described. The implant body 808 may further include the strain reliefs 852 positioned and configured as shown. There may be first and second strain reliefs 852 positioned on a distal side of the body 808 near the neck 850. There may also be third and fourth strain reliefs 852 positioned on the proximal side of the body 808 as oriented and located radially more inward than the outer strain reliefs 852 near the neck. The strain reliefs 852 may be recesses in the body 808 that extend circumferentially along the body 808. For example, the two outer strain reliefs 852 (as oriented in the figure) may be part of the same recess that extends circumferentially around the body 808. Similarly, the two inner strain reliefs 852 (as oriented in the figure) may be part of the same recess that extends circumferentially around the body 808. There may be more or fewer than the four strain reliefs 852 shown. The foregoing is one example and other suitable configurations may be implemented.

The strain reliefs 852 may facilitate absorbing side loading forces on the neck 850. Such forces may be due to for example incorrect or misaligned insertion of the implant 2A, a misaligned or off-angle burr hole, etc. Such forces may induce loading and/or deformation on the implant body 808 which may for example deform the diaphragm 820. The strain reliefs 852 may assist with preventing such forces from affecting the diaphragm 820 and/or other parts of the implant or implant body 808.

Figure 22B:
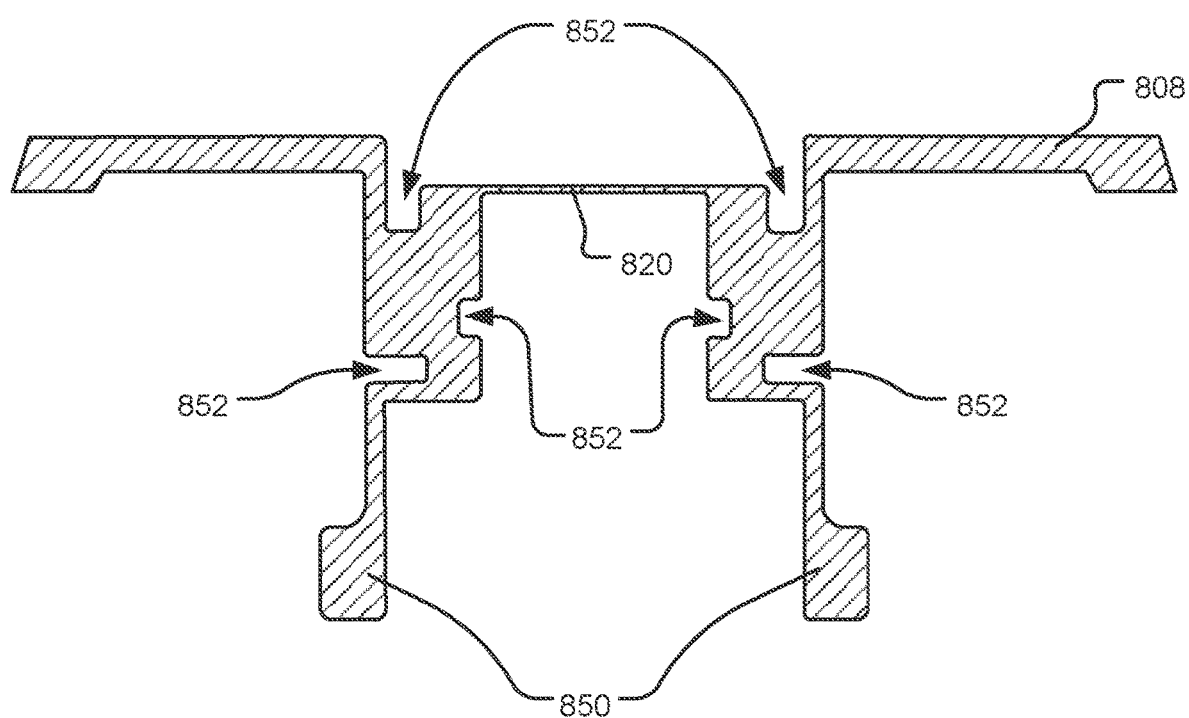

FIG. 22B illustrates a partial cross-section view of another embodiment of the implant body 808 that may be used with the various implants described herein. As shown, the strain reliefs 852 may be located in various locations. There may be a strain relief or reliefs 852 located along the outside of the neck 850, which may be for example a recess, such as the recess 19. The two strain reliefs 852 shown along the outside of the neck may be part of the same recess extending circumferentially around the neck 850. Similarly, there may be a strain relief or reliefs 852 located along the inside of the neck 850, which may be for example a recess. The two strain reliefs 852 shown along the inside of the neck may be part of the same recess extending circumferentially around the interior of the neck 850. Further, there may be a strain relief or reliefs 852 located along a top surface of the implant body 808 as oriented in the figure, which may be for example a recess. The two strain reliefs 852 shown at the top surface of the implant body 808 may be part of the same recess extending circumferentially around a diaphragm 820. This is merely an example of an implant body 808 and neck 850 having strain reliefs 852, and other configurations may be implemented.

Figure 23A:
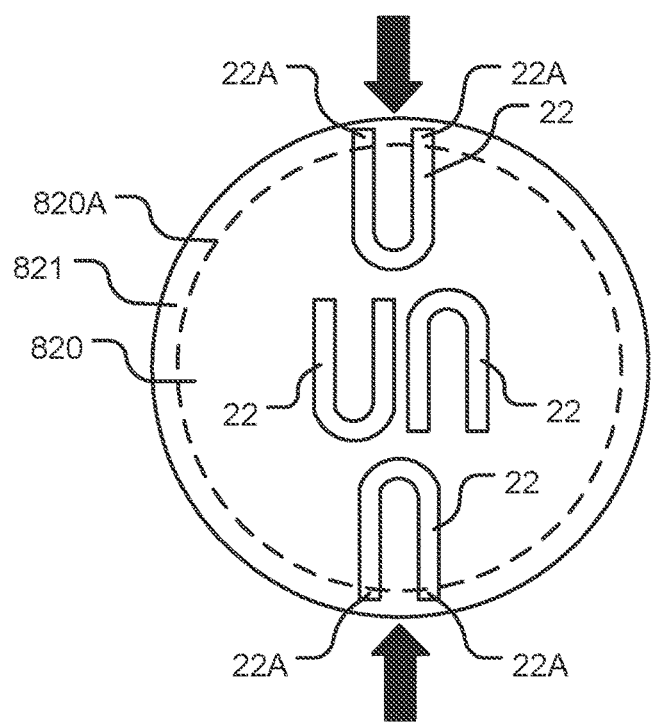
FIGS. 23A-23B illustrate example layouts of sensors that may be used with the various implants described herein.
Figure 23B:
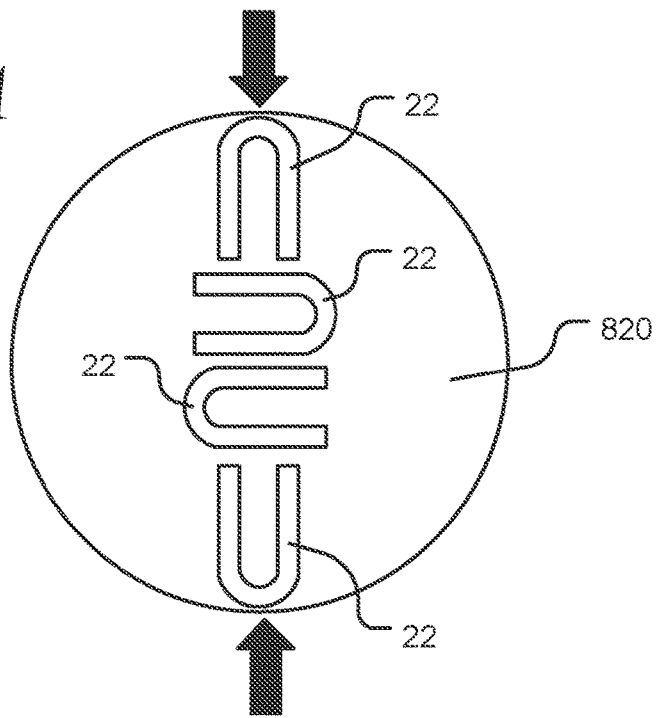

FIGS. 23A-23B illustrate example layouts of the sensors 22 that may be used with the various implants described herein. In some embodiments, as mentioned, the sensors 22 may be strain gages. As shown, the sensors 22 may be arranged generally linearly from one side of the diaphragm 820 to the opposite side. There may be four sensors 22. In some embodiments, there may be one, two, three, five or more sensors 22. The generally linear arrangement of the sensors 22 may reduce interference with the sensors due to various loading conditions. For example, having strain gages aligned in these directions will reduce or remove interference with signals from the strain gages if loads are applied in the directions as indicated by the arrows or if hoop strain is induced on the diaphragm 820 due to induced loads. In some embodiments, a circuit with a Wheatstone bridge arrangement may be used with the sensors 22, such as strain gages, in which case the arrangements of the sensors 22 as shown will induce bridge auto-compensation, whereby all arms of the Wheatstone bridge are affected evenly and symmetrically with hoop strains or side loadings. Thus, the arrangements of the sensors 22 shown may allow for more reliable and robust measurements of pressure with the diaphragm 820.

In some embodiments, the sensors 22 are arranged relative to a witness line 820A, as shown in FIG. 23A. The witness line 820A may be helpful because the outer boundaries of the diaphragm 820 may not be apparent from the side of the diaphragm 820 on which the sensors 22, such as strain gages, are located. The line 820A may thus be etched or otherwise indicated on the side of the implant body to which the sensors 22 are coupled to indicate the location of the outer boundary of the diaphragm 820. In some embodiments, the witness line may be projected onto the part during manufacturing, assembly, insertion of a reticle into a microscope, etc. There may thus be an outer region 821 outside the diaphragm 820 and also defined by the line 820A. Further, the sensors 22 may be positioned so that only particular portions of the sensors 22 are located in this outer region 821 while other portions are on the diaphragm 820. For example, the part of the strain gages that sense strain, which may be called the active regions, may be located over the diaphragm 820. Further, the part of the strain gages that are inactive or that do not sense strain, which may be called the pads 22A, may be located over the outer region 821. The pads 22A are inactive and provide a coupling for an electrical connection. A circular diaphragm has its highest strain at the very outer edge, i.e. along the witness line 820A. Therefore, to optimize sensitivity, the strain gages near the witness line 820A are located so that the pads 22A are slightly outside of the diaphragm 820 region, so that the active region of the strain gages are located at the outer border of the diaphragm 820.

A person/one having ordinary skill in the art would understand that information and signals can be represented using any of a variety of different technologies and techniques. For example, data, instructions, commands, information, signals, bits, symbols, and chips that can be referenced throughout the above description can be represented by voltages, currents, electromagnetic waves, magnetic fields or particles, optical fields or particles, or any combination thereof. A person/one having ordinary skill in the art would further appreciate that any of the various illustrative logical blocks, modules, processors, means, circuits, and algorithm steps or blocks described in connection with the aspects disclosed herein can be implemented as electronic hardware (e.g., a digital implementation, an analog implementation, or a combination of the two, which can be designed using source coding or some other technique), various forms of program or design code incorporating instructions (which can be referred to herein, for convenience, as "software" or a "software module"), or combinations of both. To clearly illustrate this interchangeability of hardware and software, various illustrative components, blocks, modules, circuits, and steps or blocks have been described above generally in terms of their functionality. Whether such functionality is implemented as hardware or software depends upon the particular application and design constraints imposed on the overall system. Skilled artisans can implement the described functionality in varying ways for each particular application, but such implementation decisions should not be interpreted as causing a departure from the scope of the present disclosure.

The various illustrative logical blocks, modules, and circuits described in connection with the aspects disclosed herein and in connection with the figures can be implemented within or performed by an integrated circuit ("IC"), an access terminal, or an access point. The IC can include a general purpose processor, a digital signal processor ("DSP"), an ASIC, a FPGA or other programmable logic device, discrete gate or transistor logic, discrete hardware components, electrical components, optical components, mechanical components, or any combination thereof designed to perform the functions described herein, and can execute codes or instructions that reside within the IC, outside of the IC, or both. The logical blocks, modules, and circuits can include antennas and/or transceivers to communicate with various components within the network or within the device. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration. The functionality of the modules can be implemented in some other manner as taught herein. The functionality described herein (e.g., with regard to one or more of the accompanying figures) can correspond in some aspects to similarly designated "means for" functionality in the appended claims.

If implemented in software, the functions can be stored on or transmitted over as one or more instructions or code on a computer-readable medium. The steps or blocks of a method or algorithm disclosed herein can be implemented in a processor-executable software module which can reside on a computer-readable medium. Computer-readable media includes both computer storage media and communication media including any medium that can be enabled to transfer a computer program from one place to another. A storage media can be any available media that can be accessed by a computer. By way of example, and not limitation, such computer-readable media can include RAM, ROM, EEPROM, CD-ROM or other optical disk storage, magnetic disk storage or other magnetic storage devices, or any other medium that can be used to store desired program code in the form of instructions or data structures and that can be accessed by a computer. Also, any connection can be properly termed a computer-readable medium. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm can reside as one or any combination or set of codes and instructions on a machine readable medium and computer-readable medium, which can be incorporated into a computer program product.

It is understood that any specific order or hierarchy of steps or blocks in any disclosed process is an example of a sample approach. Based upon design preferences, it is understood that the specific order or hierarchy of steps or blocks in the processes can be rearranged while remaining within the scope of the present disclosure. The accompanying method claims present elements of the various steps or blocks in a sample order, and are not meant to be limited to the specific order or hierarchy presented.

Various modifications to the implementations described in this disclosure can be readily apparent to those skilled in the art, and the generic principles defined herein can be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "example" is used exclusively herein to mean "serving as an example, instance, or illustration." Any implementation described herein as "example" is not necessarily to be construed as preferred or advantageous over other implementations.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system components in the implementations described above should not be understood as requiring such separation in all implementations, and it should be understood that the described program components and systems can generally be integrated together in a single software product or packaged into multiple software products. Additionally, other implementations are within the scope of the following claims. In some cases, the actions recited in the claims can be performed in a different order and still achieve desirable results.

What is claimed is:

1. An apparatus for measuring intracranial pressure (ICP), comprising:
   a body having a proximal side and a distal side with at least one standoff coupled with and extending distally away from the body, wherein a distal end of the at least one standoff is configured to support the body against a patient;
   a pressure conduction catheter having a proximal end and a distal end, the proximal end coupled with the body, wherein the distal end is configured to extend into a brain through a hole in a skull of the patient;
   at least one sensor configured to obtain data indicative of changes in ICP at the distal end of the catheter; and
   wherein the catheter defines a lumen configured to fill with media to provide a pressure conductive path following implantation through the hole.

2. The apparatus of claim 1, wherein the distal end of the catheter further includes a plurality of ports, and the at least one sensor is configured to obtain the data indicative of changes in ICP at the plurality of ports at the distal end of the catheter.

3. The apparatus of claim 1, wherein the at least one standoff extends circumferentially about a central axis.

4. The apparatus of claim 1, wherein the at least one standoff comprises a radially inner portion and a radially outer portion, and wherein the radially outer portion extends farther distally than the radially inner portion.

5. The apparatus of claim 1, wherein the at least one sensor is configured to detect deformation of a diaphragm configured to deform in response to changes in ICP.

6. The apparatus of claim 5, wherein the diaphragm is positioned at the proximal end of the pressure conduction catheter.

7. The apparatus of claim 5, wherein the diaphragm and the body are unibody.

8. The apparatus of claim 1, the body further comprising a neck extending distally, the neck comprising a recess extending circumferentially along the neck.

9. The apparatus of claim 1, further comprising a processor configured to receive the obtained data and determine the ICP based at least in part on the obtained data.

10. The apparatus of claim 1, wherein the media comprises a gas or liquid.

11. The apparatus of claim 1, wherein the distal end of the catheter comprises a barrier.

12. The apparatus of claim 1, wherein the catheter comprises a plurality of ports extending at least partially along a length of the catheter so that the data indicative of changes in ICP at the distal end of the catheter is based at least on the sum of pressure at all depths of the brain that the plurality of ports traverses.

13. The apparatus of claim 12, wherein the plurality of ports extend along the entire length of the catheter.

14. The apparatus of claim 1, wherein the catheter comprises a plurality of ports extending along a length of the catheter, and the catheter is configured to be cut in length for customization based on a particular patient.

15. The apparatus of claim 1, wherein a distal-facing end of the catheter is closed.

16. The apparatus of claim 15, wherein the catheter comprises an endpiece that closes the distal end of the catheter.

17. An apparatus for measuring intracranial pressure (ICP), comprising:
 a body having a proximal side and a distal side with at least one standoff coupled with and extending distally away from the body, wherein a distal end of the at least one standoff is configured to support the body against a patient;
 a pressure conduction catheter having a proximal end and a distal end, the proximal end coupled with the body, wherein the distal end is configured to extend into a brain through a hole in a skull of the patient;
 at least one sensor configured to obtain data indicative of changes in ICP at the distal end of the catheter;
 a diaphragm configured to deform in response to changes in ICP, wherein the diaphragm is positioned at the distal side of the body; and
 a recess in the distal side of the body and extending circumferentially about the diaphragm.

18. The apparatus of claim 17, wherein the recess is in a proximal side of the distal side of the body.

19. The apparatus of claim 17, wherein the recess is in a distal side of the distal side of the body.

20. The apparatus of claim 17, wherein the catheter comprises a plurality of ports extending at least partially along a length of the catheter.

21. The apparatus of claim 17, wherein the distal-facing end of the catheter is closed.

* * * * *